(12) United States Patent
Power

(10) Patent No.: US 7,601,509 B2
(45) Date of Patent: Oct. 13, 2009

(54) BIOTYPE DIETS SYSTEM: PREDICTING FOOD ALLERGIES BY BLOOD TYPE

(76) Inventor: Laura W. Power, 1952 Dundee Rd., Rockville, MD (US) 20850

(*) Notice: Subject to any disclaimer, the term of this patent is extended or adjusted under 35 U.S.C. 154(b) by 385 days.

(21) Appl. No.: 11/178,666

(22) Filed: Jul. 12, 2005

(65) Prior Publication Data

US 2006/0013773 A1   Jan. 19, 2006

Related U.S. Application Data

(60) Provisional application No. 60/587,827, filed on Jul. 15, 2004.

(51) Int. Cl.
*G01N 33/00* (2006.01)
*G01N 33/543* (2006.01)

(52) U.S. Cl. .................. 435/7.21; 436/501; 436/518; 422/50; 422/61; 424/9.1

(58) Field of Classification Search ............... None
See application file for complete search history.

(56) References Cited

U.S. PATENT DOCUMENTS

| | | |
|---|---|---|
| 4,606,555 A | 8/1986 | Adams |
| 4,950,164 A | 8/1990 | Lennon-Thompson |
| 4,976,622 A | 12/1990 | Clark |
| 5,595,772 A | 1/1997 | Wurtman et al. |
| 6,291,533 B1 | 9/2001 | Fleischner |
| 6,503,529 B1 | 1/2003 | Fleischner |
| 6,632,622 B2 | 10/2003 | Jaffe |
| 6,635,015 B2 | 10/2003 | Sagel |

OTHER PUBLICATIONS

Kelso and Armelagos, SW Lore, 1963 XXIX (2), pp. 44, 46-47.*
Kelso & Armelagos, Nutritional Factors as Selective Agencies . . . , SW Lore, 1963; XXIX(2): p. 44, 46-47.
Weisberg & Christiano, The Answer Is In Your Blood Type, Miami: Personal Nutrition, 1997: pp. ToC, 129+135.
James D'Adamo, One Man's Food . . . , New York: Richard Marek, 1980, pp. ToC, 40+48.
Peter D'Adamo, Eat Right For Your Type, New York: Putnam, 1996, pp. ToC, 96-97, 148-149, 252.
Laura Power, Biotype Diet System, Journal of Nutritional & Environmental Medicine, 2007, iFirst, pp. Abstract, 8-10.
Nachbar & Oppenheim, Lectins In the United States Diet, AJCN, 1980, vol. 31, pp. Abstract, 2340-2343.
Metcalfe & Sampson, Workshop, JACI, Supplement, 1990, vol. 86, No. 3, Part 2, pp. Title, 436-437.
Annys Shin, Food Allergies Trigger Multibillion-Dollar Specialty Market, The Washington Post, Jun. 8, 2008, pp. 1 & 8.
Kontis et al, Food Allergy and the Use of in Vitro Tests for Allergen-Specific IgE . . . , Journal of Clinical Ligand Assay, 2005, vol. 8, No. 2, pp. 88-99.
Hamilton Dixon, Treatment of delayed food allergy based on specific IgG RAST testing, Otolaryngology . . . , 2000, vol. 123, No. 1, Part 1, p. 48-54.
Laura Power, Biotype Diets System . . . , Journal of Nutritional & Environmental Medicine, 2007, iFirst, pp. 1-11. [Full article.].

* cited by examiner

*Primary Examiner*—Lisa V Cook

(57) ABSTRACT

The invention is a diet-typing system for humans, including novel methods for diagnosis and treatment of food allergies and hypersensitivities. The diagnostic method correlates blood types (immunologically reactive antigens on RBC, skin and membranes) to four kinds of food allergies/hypersensitivities (IgE antibodies, IgG antibodies, T-cells, and Lectins). The results are used to identify and predict food allergies and hypersensitivities for six biological types (blood types A1, A2, B, O, A1B, and A2B), plus diet modifications for three subtypes (blood type Rh-negative, males and females). The treatment method uses the results to make food recommendations (to eat, limit, or avoid), based on the strength or classification of allergy scores, to mitigate the risk of food allergies and hypersensitivities in future persons. The diet-typing system presents the results on six diet cards, one for each blood type. The methods and resulting diets are unique, and differ substantially from prior inventions.

20 Claims, 5 Drawing Sheets

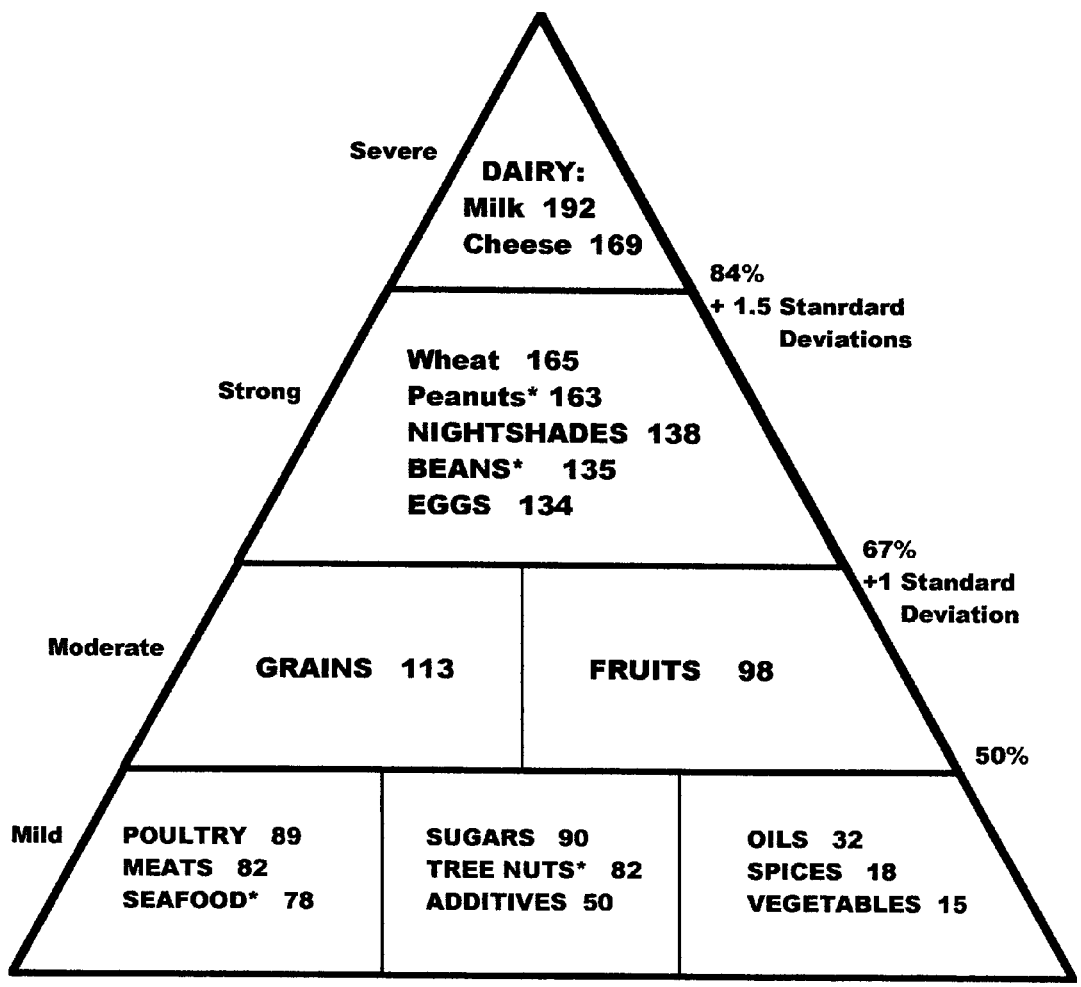

FIG. 1
Food Allergy Pyramid

The Pyramid represents the relative allergenicity of 15 food groups, ranked from highest to lowest. The total score for each food group is the sum of 4 kinds of allergy tests (IgE, IgG, Lectins, T-cells), each of which has been converted to percentages. Lectins include only pan-lectins that react with all blood types, and are scored at 25%. Scores for vegetables, sugars, oils, spices, and additives are based on T-cell testing only (x2). *Note: Nuts, beans and seafood can cause violent, life-threatening reactions in some people, but are not reactive for most people.

The Diet Compass

The 5 Biotype Diets (for blood types A1, A2, B, O, AB) are superimposed upon a globe and cross (compass), and positioned according to each blood type's highest frequency, and titled according to the respective geographic locations (Europe, Arctic, Asia, Mid-East, Tropics).

BIOTYPE DIETS SYSTEM

A set of 6 diet cards, ranging in size from 7x9 to 8.5x11, preferably laminated. Each card contains a diet for one blood type. Each side of the card contains 5 columns, one for each food group(s). The top of each column identifies food allergens, while the bottom identifies safe foods. Food allergens are ranked by Classes 1-5 plus L (for lectins).

FIG. 4a
BIOTYPE B: THE ASIAN DIET (Side 1)

| DAIRY-EGGS | MEATS | SEAFOOD | GRAINS | SUGAR-OILS |
|---|---|---|---|---|
| ALLERGIES | ALLERGIES | ALLERGIES | ALLERGIES | ALLERGIES |
| DAIRY:<br>Butter - 3<br>Casein - 3<br>Cheese - 3<br>Milk, Cow - 3<br><br>EGGS:<br>Egg White - 3<br>Egg Yolk - 3 | Pork - 1<br>Beef - 2<br>Chicken -3 | Clam - 1<br>Shrimp - 1<br>Salmon - 1 + L<br>Tuna - 1 + L<br><br>Crab - L<br>Halfmoon Fish - L<br>Opaleye Fish - L<br>Salmon Caviar - L<br>Trout Caviar - L<br>Snakes - L<br>Turtle - L<br>(Western Painted) | Oats - 1<br>Rice - 1<br>Corn - 3<br>Rye - 2<br>Wheat - 2 | Sugar, Beet - 4<br>Sugar, Cane - 4<br>Sugar, Corn - 4<br><br>OILS:<br>Cottonseed-2 |
| SAFE | SAFE | SAFE | SAFE | SAFE |
| Yogurt | Deer<br>Duck<br>Goose<br>Lamb<br>Rabbit<br>Turkey<br>Wild Fowl<br>Wild Game | Anchovy<br>Bass<br>Cod<br>Flounder<br>Haddock<br>Lobster*<br>Oyster<br>Perch<br>Sardine<br>Scallop<br>Sea Urchin*<br>Snapper<br>Turbot | Amaranth<br>Barley<br>Buckwheat<br>Millet<br>Triticale | SUGARS:<br>Honey<br>Maple<br>Molasses<br><br>OILS:<br>Cod Liver<br>Grapeseed<br>Linseed-Flax<br>Primrose<br>Safflower<br>Walnut |

ALLERGY CLASSES: 1 = Mild, limit to twice/week. 2 = Moderate, limit to once/week.
3 = Strong, avoid.  4 = Severe, avoid.  L = B-Lectin, strong, avoid.

*Pan-Lectins that react mildly with all ABO cells.

FIG. 4b
BIOTYPE B: THE ASIAN DIET  (Side 2)

| NUTS | BEANS | VEGETABLES | FRUITS | HERB-SPICES |
|---|---|---|---|---|
| ALLERGIES | ALLERGIES | ALLERGIES | ALLERGIES | ALLERGIES |
| Almond-1<br>Cashew – 1<br>Peanut – 4 + L<br>Sesame Seed – L | Coffee – 2<br>Chocolate – 3<br>Soybean – 4 + L<br>Black Eyed Peas – L<br>Castor Bean – L<br>Cocoa Bean – L<br>Field Bean – L<br>Mung Bean – L<br>(sprouts) | Bell Pepper-1<br>Eggplant – 2<br>Potato – 1<br>Tomato – 2<br>Alfalfa – L<br>Cucumber – L<br>(wild type)<br>2 Mushrooms – L:<br>Hygrophorus-<br>Hypothejus &<br>MarasmiuS-<br>Oreades | Apple-1<br>Cantaloupe – 2<br>Cranberry-2<br>Pineapple – 1<br>Banana – 1<br>Grapes – 2<br>Orange – 2<br>Strawberry – 1<br>Melon– L<br>(Bitter Pear)<br>Pomegranate – L | Baking Powder-1<br>MSG – 3<br>Tea-2<br>Yeast – 3 +L<br><br>*Coronilla* Herb – L<br>*Evonymous –<br>Europaeus* – L<br>Licorice, Indian – L |
| SAFE | SAFE | SAFE | SAFE | SAFE |
| Brazil<br>Caraway*<br>Chestnut<br>Coconut*<br>Filbert<br>Hazelnut*<br>Macadamia<br>Pecan<br>Pistachio<br>Poppy<br>Pumpkin*<br>Sunflower<br>Walnut* | Broad Bean<br>Carob<br>Cola<br>Fava Bean<br>Garbanzo<br>Jack Bean*<br>Kidney Bean*<br>Kintoki Bean*<br>Lentil*<br>Lima Bean<br>Locust Bean*<br>Navy Bean*<br>Peas*<br>Pinto Bean*<br>Processor*<br>Tofu<br>Wax Bean* | Artichoke<br>Asparagus*<br>Avocado<br>Beet<br>Broccoli<br>Brussel Sprout<br>Cabbage<br>Carrot<br>Chicory*<br>Cauliflower<br>Celery*, Chive<br>Cucumber*<br>Eggplant<br>Lettuce Leek<br>Olive<br>Parsnip<br>Radish*<br>Rhubarb<br>Rutabaga*<br>Spinach, Squash<br>Swiss Chard*<br>Turnip, Yam | Apricot<br>Blackberry<br>Blueberry<br>Boysenberry<br>Cherry*<br>Currant*<br>Cranberry*<br>Date<br>Fig<br>Grapefruit<br>Lemon<br>Lime<br>Kiwi<br>Mango<br>Nectarine<br>Papaya<br>Peach<br>Pear, Plum<br>Raspberry<br>Tangerine<br>Watermelon | Allspice<br>Basil-Sage<br>Chili<br>Cilantro<br>Cinnamon<br>Clove, Curry<br>Dill<br>Garlic<br>Ginger<br>Horseradish<br>Kelp, Mace<br>Mustard<br>Nutmeg*<br>Onion<br>Oregano<br>Paprika<br>Peppermint*<br>Pimiento<br>Rosemary<br>Spearmint<br>Thyme<br>Vanilla |

BIOTYPE DIETS SYSTEM: PREDICTING FOOD ALLERGIES BY BLOOD TYPE

CROSS-REFERENCE TO RELATED APPLICATIONS:

This application claims priority to the Provisional Patent Application No. 60/587,827, filed Jul. 15, 2004.

BACKGROUND OF TIE INVENTION

1. Field of Invention

This invention proposes a food-allergy-typing system for diagnosis and treatment; specifically these correlate blood types to food allergies and food hypersensitivities.

2. Prior Art

The problem with most diets is that not all people can eat the same foods due to digestive differences, and food intolerances, allergies and hypersensitivities. Allergy or hypersensitivity testing for individuals can be time-consuming, expensive, unreliable, dangerous, or difficult to obtain. Commercial and published diet systems are abundant, but confusing, and often inaccurate or inappropriate. A solution lies in the fact that humans exhibit biological individuality, patterns and types with regard to both physiology and diet. Therefore, a scientifically based diet-typing system is needed that matches types of people to types of diets. This could reduce food allergies for millions of people without undergoing allergy testing.

A patent search shows that there are no patented diet-typing systems per se. A review of the literature reveals that there are no scientifically based diet-typing systems; but there are three authors of popular books reporting similar systems.

Two authors of popular diet-typing systems: James d'Adamo and Peter d'Adamo have published popular books with only four diets for four blood types (A, B, O, AB). James d'Adamo published *One Man's Food* (1980). Peter d'Adamo (his son) published *Eat Right For Your Type* [Putnam, 1996]. However, their system does not employ blood subtypes A1, A2, A1B, A2B, Rh-positive, or Rh-negative, which limits their specificity. Their methods for determining diets are based on observation of patients, and not on objective criteria such as food allergies or food hypersensitivities, which limits their accuracy. Peter d'Adamo's book mentions food lectins. (See below). However, his list of lectins contradicts the known scientific literature. Furthermore, the foods for each of their diets are substantially different than those of my invention. In these five major ways my invention differs from their diet-typing system.

A third popular book matches four blood types with macronutrients (carbohydrates, proteins, fats), blood cholesterol levels, and with morbidity and mortality rates, and makes diet recommendations. No food allergies or hypersensitivities are mentioned, nor are sub-blood types. [S M Weissberg & J Christiano, *The Answer Is In Your Blood Type*, by Personal Nutrition, U.S.A., 1999].

Several diverse scientific articles and books report on food lectins. These are protein allergens in certain foods that bind to specific ABO blood type antigens. However, these consist of scattered references; no one list is complete, nor do any of these describe a diet-typing system. Most were originally intended for commercial blood bank typing. [M S Nachbar & J D Oppen-heim, *Lectins in the United States Diet*, American Journal of Clinical Nutrition. 1980: Vol. 33.]

Blood types have been correlated with kinds of diseases, including aero allergies. But no other studies exist which correlate blood types with food allergies. [A E Mourant, *Blood Groups and Diseases*, Oxford Univ Press, London, 1978.]

Two patents were granted that match blood types with nutrient need patterns. U.S. Pat. No. 6,291,533 B1, Sep. 18, 2001, was granted to Fleischner, entitled "Dietary Supplements For Each Specific Blood type." U.S. Pat. No. 6,503,529 B1, Jan. 7, 2003, was also granted to Fleischner, entitled "Blood type Methods and Dietary Supplements." These relate blood types with nutrients, but do not address foods, diets, allergies, or hypersensitivities.

Five patents have been granted for human "Diet Systems": U.S. Pat. No. 4,950,164 for "Diet Planning and Control System and Methods"; U.S. Pat. No. 6,635,015 for "Body Weight Management System"; U.S. Pat. No. 5,595,772 for "Composition and Methods For Losing Weight"; U.S. Pat. No. 4,976,622 A for "Diabetic Diet Plan Aid and Method"; and U.S. Pat. No. 4,606,555 A for "Diet Control Device and Method." All systems are for weight control or diabetes. None of these is a diet-typing system. None involves blood types, food allergies or food hypersensitivities.

At least one patent has been issued for an animal diet-typing system: U.S. Pat. No. 6,537,213 B2 for "Animal Health Care, Well-Being and Nutrition." The system employs a dedicated computer that types animals by species, monitors health, and recommends therapy based on nutrition.

FASEB Abstract, 1992, Laura Power & Robert Jackson. The author reported a small pilot study, which correlated ABO blood types to food allergy tests (IgE and IgG antibodies). It did not examine T-cell hypersensitivities nor lectin responses. It had inadequate numbers of subjects in each blood-type category. Only food group results were reported not specific foods: This represents an experimental phase, and differs substantially from Power's current final invention in: allergy-test criteria, number of subjects, test results, and conceptual overview.

In conclusion, so far as I am aware, no other diet system by any other inventor provides a typing system based on blood types correlated to food allergies or food hypersensitivities.

BRIEF SUMMARY OF THE INVENTION

The invention is a diet-typing system for humans, including novel methods for diagnosis and treatment of food allergies and hypersensitivities. The diagnostic method correlates blood types to four kinds of food allergies/hypersensitivities (IgE antibodies, IgG antibodies, T-cells, and Lectins). The results are used to identify and predict food allergies and hypersensitivities for six biological types (blood types A1, A2, B, O, A1B, and: A2B), plus diet modifications for three subtypes (blood type Rh-negative, males and females). The treatment method uses the results to make food recommendations (to eat, limit, or avoid), based on the strength or classification of allergy scores, to mitigate the risk of food allergies and hypersensitivities in future persons. The diet-typing system presents the results on six diet cards, one for each blood type. The methods and resulting diets are unique, and differ substantially from prior inventions.

BRIEF DESCRIPTION OF THE DRAWINGS

FIG. 1 is an illustration of the "Food Allergy Pyramid", showing a hierarchy of food allergens for all subjects.

FIGS. 4a and 4b illustrate both sides of the "Biotype B Diet" (diet card).

OBJECTS & ADVANTAGES

Figure 2:
FIG. 2 is an illustration of "The Diet Compass", showing the geographic distribution of the ABO blood types and corresponding Biotype Diets.

The object of the invention is to provide a detailed food-allergy-typing system or diet-typing system to identify and predict, and treat or mitigate the risk of food allergies in humans. The advantages are multiple:
1. It can bypass expensive, dangerous, or time-consuming allergy testing.
2. It can be easily used by millions of people without a doctor's visit.
3. It is inexpensive and easy to do, requiring only a finger-prick test for blood types ABO, A1-A2, and Rh factor.
4. It provides unique diets for each blood type, which reflect new and unexpected results.
5. It provides diets for six types of people, rather than just four.
6. It provides diet modifications for three subtypes.
7. It is based on rigorous scientific research.
8. It is highly specific, because it employs more biological types for criteria: A1, A2, B, O, A1B, A2B, Rh-positive, Rh-negative, male and female.
9. It is highly accurate, because it is based on objective testing, using all four kinds of food allergies and hypersensitivities: IgE antibodies, IgG antibodies, T-cells, and lectins.
10. It is very precise, because clinical categories are based on standard deviations, and correspond well with standard laboratory ranges for food allergies and hypersensitivities.
11. It provides The Diet Compass to summarize and illustrate the diet types.
12. It provides a Food-Allergy Index to compare specific food allergens for all people.
13. It provides a Food-Allergy Pyramid to show a hierarchy of food allergens.
14. In summary it is a significant improvement on past diet-typing systems.

DETAILED DESCRIPTION OF THE INVENTION
PREFERRED EMBODIMENTS

The following three embodiments of the invention describe in detail: (1) A diagnostic method for food allergies and hypersensitivities, or of identifying and predicting the potential or propensity for these. (2) A treatment method for food allergies and hypersensitivities, or to mitigate the risk of these. And (3) a diet-typing system that contains the details of six diets, plus modifications for sub-types, and which is recorded on cards or another medium.

1. Diagnostic Method for Food Allergies

The first embodiment of the invention, and most preferred, is a diagnostic method that identifies food allergies, or food hypersensitivities, or adverse immune responses to foods in human subjects, and uses this to formulate a "Food-Allergy-Typing System" or "Food Allergy Index", for the purpose of predicting potential food allergens in future subjects, wherein-said method comprises:
(a) Identifying human subjects with specific ABO or Rh blood types, and optionally gender, and selecting for at least two of these blood types;
(b) Generating immune response test scores on subjects to various foods, which are indicative of food allergies (IgE) or food hypersensitivities (IgG or T-Cell), and optionally to use these with known hypersensitivities to food lectins;
(c) Correlating the blood types (and optionally gender) from step (a) to the immune response test scores from step (b) using appropriate statistical methods to develop data;
(d) Interpreting said data to formulate a "Food-Allergy-Typing System", which identifies allergenic foods for each blood type, and optionally gender, or a "Food-Allergy Index" which identifies and ranks allergenic foods for persons of all blood types.

Preferences For Diagnostic Method

Preferably the diagnostic method is based on a descriptive study, of the cross-sectional survey or correlational type. This means that it analyzes the prevalence of a disease (several kinds of food allergies), and correlates them statistically to variables that are unaltered over time (blood types). (Hennekens & Buring, *Epidemiology In Medicine*, Little Brown, Boston, 1987.)

Blood Types

The blood types can be any that are known in the art. These include: ABO, Rh, MNS, Duffy, Kell, Kidd, Lewis, P, Diego, Indian, Lutheran, and others. (Daniels, *Blood Reviews* 13, 14-35, 1999.) Preferably, the blood types are selected from the group consisting of A1, A2, B, O, A1B, A2B, Rh-positive, and Rh-negative. Preferably, the food-allergy-typing system contains food allergy information on subjects of at least two blood types, more preferably on at least five blood types, and still more preferably on at least seven blood types. The system can also contain food allergy information on males only on females only, or both males and females. Preferably each group should consist of at least 15 subjects, and more preferably 30 to 300 subjects, to ensure adequate numbers for statistical evaluation. (P D Issit & C H Issit, *Applied Blood Group Serology*, Biological Corp of America, West Clester, Pa., 1981).

Immune Responses

Subjects suffering from food allergies or hypersensitivities often exhibit elevated IgE and/or IgG levels. Preferably measuring the levels of these immunoglobulin (antibodies) would be used as an indicator of such allergies or hypersensitivities. This is usually done by the Fadal-Nalebuff Modified RAST or by ELISA. [Nalebuff, Fadal & Ali. The Study of IgE in the diagnosis of allergic disorders in an otolaryngology practice, IN Otolaryngol Head Neck Surgery. May-June 1979;87 (3): 351-8.] Hypersensitivity of subjects to specific foods can also be assessed by T-cell blastogenesis assay, as in the method of the ELISA/ACT™ LRA [U.S. Pat. No. 6,632,622, the disclosure of which is incorporated herein by reference]. Hypersensitivities to known blood-type specific lectins can be obtained from the prior art. Other methods of assessing food allergies can be used as are known in the art.

Foods Tested

Preferably the number of foods tested should be at least 30, and more preferably 100 to 300 foods, to support proper statistical evaluation of data. These foods can include any foods or food additives that are eaten by humans. Most preferably these would include the following foods: butter, casein, cheese, cow milk, goat milk, yogurt, egg white egg yolk, beef, chicken, deer, duck, lamb, pork, rabbit, turkey, crab, lobster, shrimp, clam, oyster, scallop, anchovy, bass, catfish, cod, flounder-sole, haddock, perch, red snapper, salmon, sardine, shark, swordfish, trout, tuna, turbot, amaranth, barley, buckwheat, corn, millet, oats, rice, rye, triticale, wheat, alfalfa, almond, anise, Brazil, caraway, cashew, chestnut, coconut, filbert, hazelnut, macadamia, pecan pistachio, poppy pumpkin, sesame, sunflower, walnut, black-eyed peas, carob, chocolate, coffee, COLA, garbanzo beans, kidney beans, lentils, lima beans, navy beans, peanuts, peas, pinto beans, soy beans string beans, tofu, artichoke, asparagus, avocado, beet, broccoli, brussel sprouts, cabbage, carrot, cauliflower, celery, chive, cucumbers, endive, iceberg lettuce, leek, mushroom, olive, parsnip, radish, red leaf lettuce, rhubarb, romaine lettuce, rutabaga, spinach, squash, turnip, yam, bell pepper, cayenne pepper, eggplant, potato, tomato, codliver oil, cottonseed oil, grapeseed oil, hydrogenated oil, linseed oil, primrose oil, safflower oil, walnut oil, apple, apricot, banana, blackberry, blueberry, boysenberry, cantaloupe, cherry, cranberry, currant, date, fig, grape, grapefruit, kiwi, lemon, lime, mango, nectarine, orange, papaya, peach pear, pineapple, plum, raspberry, strawberry, tangerine, watermelon, beet sugar, cane sugar, corn syrup, honey, maple syrup, molasses, allspice, basil-sage, bay leaf, chili, cinnamon, clove, curry, dill, garlic, ginger, horseradish, kelp, mace, mustard, nutmeg, onion, oregano, paprika, parsley, pepper, peppermint, pimiento, rosehip, rosemary, spearmint, tea, thyme, and vanilla. These would also include the following food additives: aspartame, baking powder, BAKING SODA, BHT-BHA, food coloring, gin, hops, malt, MSG, nitrates, saccharin, sodium benzoate, sulfites, tapioca, and yeast These would also include other foods containing lectins: Beans (African yam, castor, field, hyacinth, mung, tora, winged), brown trout, CORNFLAKES, escargot, garfish, horse gram, moluccella seeds, Product 19, Total cereal, soy sprouts, western painted turtle, common vetch, white croaker fish, coronilla herb, Evonymus Europaeus (butter dye), halfmoon fish, Indian licorice, bitter pear melon, opaleye fish, pomegranate, snake, salmon & trout caviar, asparagus pea, Australian catfish, eels, gorse, halibut, and lotus.

Statistical Analysis

Statistical methods to be used in accordance with the invention include: the statistical correlation of blood types and gender to test scores for specific food allergens or food. hypersensitivities, which are determined by means of the antibody titers (IgE and IgG), and percentage of reactive subjects (T-Cell tests). Preferably, the presence or absence of said correlation is determined using ANOVA, MANOVA, or non-parametric methods to determine p values, which is known to persons skilled in the art of statistical analysis. The p value is set at <0.05, and optionally at <0.07. In the case of lectins, a positive haemagglutination reaction is required. [Sokal & Rohlf, *Introduction to Biostatistics*, Freeman, N.Y., 1987.]

Interpreting Data

The preferred method for interpreting the data includes:

(a) Identifying patterns in food allergies relative to blood types or gender is determined by the strength of the reactions (mean test scores) and by statistical significance (p values).

(b) Establishing classes for the degree of human clinical immune reactivity to foods is problematic in three ways: (1) assigning classes to frequency distributions (ranges) of continuous variables is arbitrary, (2) groups have less extreme ranges than individuals, and (3) the frequency distribution represents a range of healthy to unhealthy food reactions, rather than bivariate normal distribution. Therefore, the preferred method of classification is to apply non-bivariate divisions to the distribution of test scores in each study. Hence the lower ⅓ of food scores may be designated as non-reactive (0-33%), the middle ⅓ designated as equivocal (34% -67%), and the upper ⅓ designated as reactive (67% -100%). And/or classifications may occur at the median (50%); and at (84%). The classifications below are comparable to conventional lab values of food allergy tests at the lower ranges, which begin at similar values for modified RAST (500 IgE and 1500 IgG). Said non-bivariate divisions may be used to establish descriptive classifications and/or numeric classifications (as shown in Table 1), with three to six categories. [Sokal & Rohlf, *Introduction to Biostatistics*, Freeman, N.Y., 1987.] [Metcalfe & Sampson, *Journal of allergy & Clinical Immunology*, Supplement, Vol, 86, No.3, Part 2, September 1990, Workshop on Experimental Methodology for Clinical Studies of Adverse Reactions to Foods and Food Additives.]

(c) Said classification (b) can be applied to the range of raw scores for both IgE and IgG, or optionally to percentages of those scores.

(d) Given that the T-cell test is qualitative, the responses are calculated based on the number of subjects reactive to a given food. The resulting percentages are ranked according to said non-bivariate divisions as in (b) above.

(e) Estimating the degree of human clinical immune reactivity to lectins is determined by assigning a percentage or Class value to lectin-containing foods. ABO-specific lectins are known to cause tissue damage, but are not as "severe" as IgE reactions. Therefore they should be assigned to the "strong" category (Class 3) at 75%. Similarly, panhemagglutinins are lectins that react with all blood types, and can cause tissue damage, but do not cause strong reactive symptoms in all people. These should be assigned to the non-reactive category (Class 0), but not to 0%, with a preferred value of 25%.

(f) Optionally the raw test scores (of IgE, IgG, T-cells, Lectins) may be converted to percentages, and the percentages of these four kinds of hypersensitivities may be summed to provide a total score for any food. A classification system (based on non-bivariate divisions) could be applied based on the range of total scores. Optionally an algorithm could be applied to all the test scores for the same purpose.

TABLE 1

Interpreting Scores for Food Allergy and Hypersensitivity Tests

| Class No. | CLINICAL CLASS: Degree of Immune Reactivity | IgE Mod RAST Antibody Titers | IgG Mod RAST Antibody Titers | T-Cell ELISA/ACT % Reactive Subjects |
|---|---|---|---|---|
| 5 | Extreme Reaction. Avoid Food | 1500 | 4800 | 100%+ |
| 4 | Severe Reaction. Avoid Food | 1250 | 4000 | 84% = 99% |
| 3 | Strong Reaction. Avoid food | 1000 | 3200 | 67%-83% |
| 2 | Moderate, Equivocal. Limit to 1X/week | 750 | 2400 | 50%-66% |
| 1 | Mild, Equivocal. Limit to 2X/week | 500 | 1600 | 34%-49% |
| 0 | Non-Reactive. Edible foods | 0 | 0 | 0%-33% |

The Food Allergy Index

The preferred method of formulating a "Food-Allergy Index" reports a hierarchy of allergenic foods for all subjects studied, and uses this to predict potential allergic reactions for subsequent subjects of all types (or optionally to use a similar method for persons of a given blood type), and comprises the following steps:

(a) Determining the scores for each food tested by each method used ((IgE, IgG, T-Cell, Lectins), then converting these scores to percentages of the score range;
(b) Combining the scores for all four immune responses measured for each food tested to obtain total scores, and assigning a "Class" to each food based on standard deviations;
(c) Arranging said total scores in a hierarchy from most allergic to least allergic, or alternately arranging these alphabetically, or arranging these by food group.

The Food Allergy Pyramid

The preferred method of formulating a "Food-Allergy Pyramid", which portrays a pictorial hierarchy of allergenic foods, comprises the following steps:
(a) Combining the Food-Allergy Index scores for specific foods into scores for food groups (such as dairy, eggs, meats, seafood, grains, nuts, beans, vegetables, nightshades, fruits, oils, sugars, herbs, additives, or other groups);
(b) Arranging said food groups and scores on a pyramid drawing, which is divided into predictive categories of mild, moderate, strong, severe (or other categories), in a hierarchy of most allergic down to least allergic;
(c) Recording said pyramid on a recording medium, of writing in any form, or electronic, or magnetic, or optical medium in any form, as shown in FIG. 1.

The Food-Allergy-Typing System

The preferred method of formulating a "Food-Allergy-Typing System" identifies food allergies for different types of subjects, then uses these to predict potential food allergens for other people of the same types, and comprises the following steps or components:
(a) Categorizing the allergenic foods to produce six food-allergy lists, each containing one set of foods for each blood type (A1, A2, B, O, A1B, A2B), or optionally five lists (with only one for type AB).
(b) In one embodiment each food allergy list contains a minimum of four foods classified as strong, severe, or extreme; in a second embodiment each food-allergy list contains a minimum of six foods classified as strong, severe, or extreme.
(c) Each food-allergy list contains certain allergenic foods or food combinations classified as extreme and/or severe that are not so classified for other blood types;
(d) Modifying said food-allergy lists with allergens relative to sub-types (blood type Rh-negative and gender).
(e) Assigning classifications to the varying degrees of allergenic reactivity of foods, named as: Class 0 (negative), Class 1 (mild), Class 2 (moderate), Class 3 (strong, or lectins), Class 4 (severe), and Class 5 (extreme), and applying these to specific ranges of raw test scores, or optionally applying these to percentages of the raw test scores.

Blood Type A1

The food allergens that have been identified for blood type A1 subjects are predictive for other type A1 persons, and preferably these comprise the following components:
(a) CLASSES 4, Severe allergens: Egg white;
(b) CLASS 3, Strong allergens: Egg yolk, cow milk, corn syrup, cheese, corn;
(c) CLASS 3, Lectins: Beans (African yam, field, lima, soy, string, tora, winged), blackberries, brown trout, giant butter clam, cornflakes, escargot, garfish, horse gram, moluccella seeds, snow white mushroom, hog peanut, Product 19, soybean sprouts, Total cereal, western painted turtle, common vetch, white croaker fish;
(d) CLASS 2, Moderate Allergens: Chocolate, eggplant, coffee, peanut, butter, casein, orange, tomato, yeast, cottonseed oil, MSG, beet sugar, potato, soy, cayenne, tea, bell pepper, food coloring;
(e) CLASS 1, Mild Allergens: Almond, cashew, rye, pineapple, wheat; banana, rice, beef, cane sugar, shrimp, baking powder, chicken, maple syrup, cantaloupe, lobster;
(e) CLASS 0, Non-Allergic: any other foods not listed as Class 1-4.

Blood Type A2

The food allergens that have been identified for blood type A2 subjects are predictive for other type A2 persons, and preferably these comprise the following components:
(a) CLASS 4, Severe Allergens: Egg white, milk;
(b) CLASS 3, Strong Allergens: Egg yolk, wheat, cheese, corn syrup, tomato, butter, casein, chocolate, corn, eggplant, yeast;
(c) CLASS 3, Lectins: Beans (African yam, field, lima, soy, string, tora, winged), blackberries, brown trout, cornflakes, escargot, garfish, moluccella seeds, 2 mushrooms (snow white, French amanita muscaria), hog peanut, Product 19, soybean sprouts, Total cereal, western painted turtle, common vetch, white croaker fish;
(d) CLASS 2, Moderate Allergens: Rye, soy, peanut, beet sugar, cane sugar, orange, cayenne, coffee, cottonseed oil, bell pepper, potato;
(e) CLASS 1, Mild Allergens: Hydrogenated oil, currant, grapefruit, tea, *Candida Albicans,* food coloring, MSG;
(f) CLASS 0, Non-Allergic: any other foods not listed as Class 1-4.

Blood Type B

The food allergens that have been identified for blood type B subjects are predictive for other type B persons, and preferably these comprise the following components:
(a) CLASS 4, Severe Allergens: Peanut, soy, beet sugar, corn syrup, cane sugar;
(b) CLASS 3, Strong Allergens: Egg white, egg yolk, casein, chocolate, cheese, milk, yeast, butter, chicken, corn, MSG;
(c) CLASS 3, Lectins: Alfalfa, castor beans, cocoa, field beans, mung bean sprouts, soy beans, black eyed peas, coronilla herb, Japanese crab, wild cucumber, Evonymus Europaeus, halfmoon fish, Indian licorice, bitter pear melon, 2 French mushrooms (*hygrophorus hypothejus, marasmius oreades*), opaleye fish, peanut, pomegranate, salmon, sesame seed, snake, salmon & trout caviar, tuna, western painted turtle, yeast;
(d) CLASS 2, Moderate Allergens: Rye, wheat, eggplant, orange, beef, coffee, cottonseed oil, cranberry, tomato, cantaloupe, tea;
(e) CLASS 1, Mild Allergens: Almond, cashew, tuna, potato, strawberry, rice, pork, pineapple, oats, apple, shrimp, baking powder, banana, bell pepper;
(f) CLASS 0, Non-Allergic: any other foods not listed as Class 1-5.

Blood Type O

The food allergens that have been identified for blood type O subjects are predictive for other type O persons, and preferably these comprise, the following components:
(a) CLASS 4, Severe Allergens: Milk, cheese, casein;
(b) CLASS 3, Strong Allergens: Egg white, egg yolk, corn syrup, beet sugar, butter, tomato;
(c) CLASS 3, Lectins: asparagus pea, Australian catfish, African yam bean, blackberries, cocoa, eels, Evonymous Europaeus (yellow butter dye), French mushrooms (*amanita muscaria*), gorse, halfmoon fish, halibut, lotus, opaleye fish, sunflower seeds;

(d) CLASS 2, Moderate Allergens: rye, wheat, banana, pineapple, chocolate, MSG, yeast, coffee, cane sugar, cottonseed oil, corn, eggplant, tea, cranberry, peanut;

(e) CLASS 1, Mild Allergens: Salmon, soy, flounder, rice, orange, oat, almond, bell pepper, potato, clam, grape, shrimp, strawberry, food coloring, cayenne, maple syrup, chicken, sodium benzoate, cantaloupe, *Candida Albicans*;

(f) CLASS 0, Non-Allergic: -any other foods not listed as Class 1-4.

Blood Type A1B

The food allergens that have been identified for blood type A1B subjects are predictive for other type A1B persons, and preferably these comprise the following components:

(a) CLASS 4, Severe Allergens: Cashew;
(b) CLASS 3, Strong Allergens: Egg white, cheese, milk, butter, casein;
(c) CLASS 3, Lectins: Hyacinth beans, and all lectins for blood types A1 and B;
(d) CLASS 2, Moderate Allergens: Egg yolk, soy, chocolate, beet sugar, tea, yeast;
(e) CLASS 1, Mild Allergens: Clam, flounder, wheat, rye, peanut, baking powder, food coloring, MSG, peanut, shrimp, anchovy, bell pepperi chicken, chocolate, coffee, corn, cottonseed oil, crab, cranberry, eggplant, honey, potato, tomato;
(f) CLASS 0, Non-Allergic: any other foods not listed for avoidance or limitation;

Blood Type A2B

The food allergens that have been identified for blood type A2B subjects are predictive for other type A2B persons, and preferably these comprise the following components:

(a) CLASSES 3, Strong Allergens: Egg white, milk, chocolate, egg yolk, soy, cheese, butter, casein;
(b) CLASS 3, Lectins: Hyacinth beans, and all lectins for blood types A2 and B;
(c) CLASS 2, Moderate Allergens: Wheat, rye, orange, flounder, rice, beet sugar, corn syrup, tea, yeast;
(d) CLASS 1, Mild Allergens: Cashews, corn, strawberry, peanut, shrimp, almond, oats, pineapple, clam, potato, pork, tuna, baking powder, food coloring, MSG, anchovy, bell pepper, chicken, coffee, cottonseed oil, crab, cranberry, eggplant, honey, potato, tomato;
(e) CLASS 0, Non-Allergic: any other foods not listed for avoidance or limitation.

Sub-Types

Preferably, the food allergens identified and predicted for specific blood types is further modified by sub-types of gender and Rh blood type as follows:

(a) Rh-negative, CLASS 5, Extreme Allergens: Peanut;
(b) Rh-negative, CLASS 4, Severe Allergens: Soy, egg white;
(c) Rh-negative, CLASS 3, Strong Allergens: Rye, milk, egg yolk, wheat, casein, cheese, milk, beet sugar, corn sugar, chocolate;
(d) Rh-negative, CLASS 2, Moderate Allergens: Cashew, almond, butter, MSG, Cottonseed oil, yeast, cane sugar, coffee, corn, orange;
(e) Males, CLASS 3, Strong Allergen: Soy;
(f) Males, CLASSES 2, Moderate Allergen: Wheat;
(e) Female Type A1's, CLASS 1: Only mild allergies to milk and cheese;
(g) Female Type B's, CLASS 1: Only mild allergies to milk, cheese and eggs.
(h) Female Type A1B's CLASS 1: Only mild allergies to milk and cheese.

Predicting Food Allergies

Preferably, the method of predicting potential food allergies or hypersensitivities involves testing a person's blood type, and employing the food-allergy index, or more preferably the food-allergy-typing system relative to blood type, to predict which foods have a high potential to be allergenic for a specific individual, and how reactive these foods might be.

2. Method of Treating Food Allergies

The second most preferred embodiment is the method of treating or mitigating the risk of food allergies or hypersensitivities, or adverse immune responses in a human subject, by employing a food-allergy-typing system or diet-typing system, which method comprises:

(a) Determining a person's ABO, A1-A2, and/or Rh blood types;
(b) Assigning a diet to said person that is specific for their blood type (and optionally gender), from a food-allergy-typing system or diet-typing system, which diet has been previously formulated to correlate blood types,(and optionally gender) with food allergies and hypersensitivities, preferably determined by. IgE, or IgG, or T-Cell, and optionally lectins;
(c) Applying treatment categories to said diet: to eat, limit or avoid foods, based on the allergy class of each food in said diet.

For example: A female with blood type O can not be given the same diet as a person of blood type A1, because the A1-female diet contains foods that are highly allergic for a type O person, such as milk, cheese, and wheat. A second example: Persons with type Rh-negative blood have an extreme allergy to peanuts, and cannot be given the diet of type A1B which allows peanut.

Preferences for Treatment Method

The preferences for the Method of Treating Food Allergies shall be the same as Embodiment 1 as to: study design, blood types, foods tested, allergy methodology, statistical analysis, interpreting data, the six diets for blood types (A1, A2, B, O, A1B, A2B), and modifications of diets for sub-types.

Treatment Categories

The preferences for applying treatment categories to said food-allergy-typing system or diet-typing system (to mitigate the risk of food allergies or hypersensitivities) are based on the following allergy classification of foods (Table 1): Class 0 Foods (negative) are safe to eat; class 1 foods (mild) should be limited to two servings per week; class 2 foods (moderate) should be limited to one serving per week; class 3 foods (strong) and class 4 foods (severe) and class 5 foods (extreme) should all be avoided. ABO specific lectins are designated as Class 3 (strong), and should be avoided. Reactive foods should be limited or avoided for a minimum of three months, more preferably for one year, most preferably for a lifetime.

Serving Sizes

"One serving per week" means a serving size established by the Code of Federal Regulations, Title 21, Chapter 1, Part 101.12, the disclosure of which is incorporated herein by reference.

Diseases Treated

Food allergies and hypersensitivities can cause many diseases. Those diseases most preferred to treat are manifest as disorders selected from the group consisting of: asthma, rhinitis, sinusitis, urticaria (hives), eczema, pruritus, otitis media, laryngeal edema, migraines, rheumatoid arthritis, celiac disease, irritable bowel syndrome, inflammatory bowel disease, nausea, vomiting, diarrhea, abdominal pain, colic, hypotension, and anaphylactic shock, [D D Metcalfe, H A Sampson, R A Simon, *Food Allergies*, by Blackwell Science, Cambridge, Mass., 1997.]

3. A Diet-Typing System

The System

Figure 3:
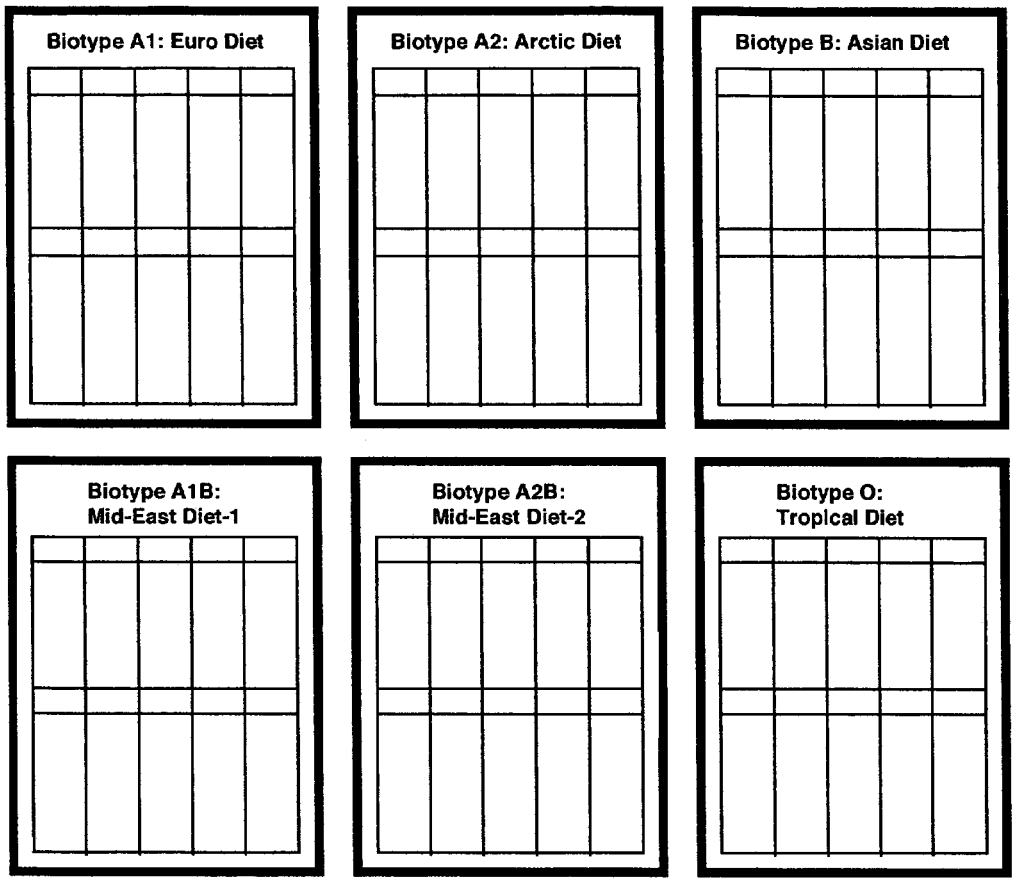
FIG. 3 illustrates the 6 diet cards for the "Biotype Diets System".

The third most preferred embodiment of the invention is the diet-typing system, optionally titled "Biotype Diets System", as seen in FIGS. 3, 4a and 4b, which comprises:

(a) 6 cards, ranging in size from 6 to 8.5 inches wide by 9 to 11 inches long, printed on two sides, preferably laminated, as shown as in FIG. 3, and shown in detail for Biotype B in FIGS. 4a and 4b;

(b) Each card contains the diet for one blood type, and shall be titled as: Biotype A1: The Euro Diet, Biotype A2: The Arctic Diet, Biotype B: The Asian Diet, Biotype O: The Tropical Diet, Biotype A1B: Mid-East Diet-1, Biotype A2B: Mid-East Diet-2, and alternately A1B and A2B may be combined onto one card titled Biotype AB: The Mid-East Diet, (c) Each biotype diet also states the modifications for subtype, based on blood type Rh-negative and gender;

(d) Said Biotype Diets shall have been determined by correlating blood types (and optionally gender) to foods tested for allergic reactivity by allergy testing, preferably by blood tests for IgE, IgG, T-cell, and optionally lectins;

(e) Each side of each card contains 5 columns, one column for each food group(s) (dairy & eggs, meats, seafood, grains, sugars & oils, nuts, beans, vegetables, fruits, herbs & spices);

(f) Each column contains one section to list allergenic foods and one section to list safe foods, or alternately allergenic foods may be printed on one side of the card and safe foods on the other side of the card;

(g) Said allergenic foods are ranked according to class: Class 1 (mild, limit to twice/week), Class 2 (moderate, limit to once/week), Class 3 (strong, avoid), Class 4 (severe, avoid), Class 5 (extreme, avoid), and ABO specific lectins are designated as Class L (3, strong), and should be avoided.

Preferences for Diet-Typing System

The preferences for the Diet-Typing System embodiment shall be the same as Embodiment 1 as to: study design, blood type, foods tested, allergy methodology, statistical analysis, interpreting data, the six diets for blood types (A1, A2, B, O, A1B, A2B), and modifications of diets for sub-types. Preferences shall be the same as Embodiment 2 for allergy treatment classifications and serving sizes.

The Diet Compass

The preferred method of representing the diet-typing system is "The Diet Compass", as shown in FIG. 2. In this diagram the 5 Biotype Diets (for blood types A1, A2, B, O, AB) are superimposed upon a globe and cross, and positioned according to each blood type's highest frequency, and titled according to the respective geographic locations (A1: Euro Diet, A2: Arctic Diet, B: Asian Diet, O: Tropical Diet, and AB: Mid-East Diet).

DETAILED DESCRIPTION OF THE INVENTION

EXAMPLES

Example 1

Experimental Methods

The study design was a descriptive study, of the cross-sectional survey and correlational types. This means that it analyzed the prevalence of a disease (several kinds of food allergies), and correlated them statistically to variables that are unaltered over time (blood types).

The results were arrived at by novel methods. From 1985 to 2000 four studies were conducted for four kinds of food allergies and hypersensitivities, representing the four Gell-Coombs Immune Responses [J. Breneman. *Basics of Food Allergy*. Thomas, Springfield, Ill., 1984.] Records were obtained from The Nutrition Clinic in Bethesda, Md. and from The Allergy & Nutrition Clinic in Falls Church, Va. Otherwise healthy patients were self-referred for nutrition or food allergy counseling. Of these the first 500 were selected who had not been avoiding suspected food allergens.

Six blood types were selected as independent variables: A1, A2, B, O, A1B, A2B. Four subtypes were also selected as independent variables: blood types Rh-positive, Rh-negative, males and females. Each subject was tested for blood type. Each subject was measured for: height, weight, pulse, and blood pressure. Body Mass Index was calculated. Each subject filled out a questionnaire that included: gender, age, and ethnic background. Each signed a consent form for the study. Each was tested for food allergies by one of the following methods.

Type 1 food allergies are immediate and mediated by IgE antibodies. They can cause asthma, rhinitis, hives, eczema, and anaphylactic shock. They were determined by a Modified RAST (Radio Allergosorbent Test) for IgE antibodies to 34 specific foods on 175 subjects. The procedure was performed by Commonwealth Medical Laboratory of Virginia, and was as follows: Ten ml of blood was drawn from the patient. Thirty-four food allergens in saline were covalently bound to a cellulose-disc. The patient's serum antibody was added, which bound to the allergen. It was then washed. A radio-labeled anti-IgE antibody was added. It was then washed and counted by a gamma counter. The modified RAST method was used; this method employs a standardized radioisotope count as a measure of the amount of antibody binding to a specific allergen. This test has CLIA approval (federal certification).

Type 2 food hypersensitivities (lectin reactions) are delayed and mediated by IgG antibodies. They can cause haemagglutination (clumping) of red blood cells and any other cells marked with ABO antigens, including intestinal cells. This can result in anemia, digestive diseases, systemic immune responses, and reportedly various autoimmune disorders. Lectin-containing foods were determined by prior art (scattered scientific references). There are currently sixty-eight ABO blood-type specific lectins in foods that have been identified.

Type 3 food hypersensitivities. (immune complexes) are delayed and mediated by IgG antibodies. They can cause deposition of immune complexes in body tissues, resulting in inflammation, and leading to inflammatory diseases. They were determined by the same laboratory and by the same methods as in Type 1 food allergies, but these measured IgG responses to 34 specific foods on 175 subjects.

Type 4 food hypersensitivities are delayed and mediated by T-Cell response. They can cause tissue inflammation and lead to inflammatory diseases. They were determined by the ELISA/ACT™ LRA (Lymphocyte Response Assay, U.S. Pat. No. 6,632,622, the disclosure of which is incorporated herein by reference), for T-Cell response to 200 foods on 150 subjects. The procedure was performed by ELISA/ACT™ BIOTECHNOLOGIES in Virginia. It is an Enzyme Linked Immunosorbent Assay/Activated Cell Test. It is a single-step solid-phase immunoassay, which combines a Lymphocyte Mitogenic Culture with a modified ELISA, to measure food-antigen-induced lymphocyte blastogenesis (primarily of T-cells). The procedure is as follows: One ounce of blood is drawn from the patient into a 30-cc syringe containing 3 cc of anticoagulant and lymphocyte culture medium. The blood is centrifuged, and the plasma incubated for 3 hours at 35 degrees C in a plastic microfiter plate containing 200+ food allergens. Where food allergens bind to sensitized lymphocytes, blastogenesis occurs, activating cell surface molecules. A chromogen is added, which produces a color when it reacts with enzymes on food-sensitized cell molecules. The response to each food is measured by visual or optical assessment, and ranked qualitatively. This test now has CLIA approval.

Example 2a

Statistical Analysis

Statistical analysis for health and demographic data was compiled in the following manner: Blood types, gender and ethnic background distributions were compared to U.S.A. distributions by chi-square analysis. Age, pulse, blood pressure, and body mass index were compared to U.S.A. population means by student's t-test. Distribution of factors between blood types were analyzed by contingency table analysis. (Data was analyzed by Stateview on Macintosh.) Results showed some statistically-significant deviations from the national norms: more rare blood types (i.e. A2, AB, B, Rh−), more females than males, an older population, normal pulse, lower blood pressure, and higher body mass index.

TABLE 2

DEMOGRAPHIC DATA FOR 3 STUDIES

| FACTORS | IgE STUDY | IgG STUDY | T-CELL STUDY | TOTAL | U.S.A. |
|---|---|---|---|---|---|
| All Subjects | 175 | 175 | 150 | 500 | |
| Blood Type A1 | 40 | 40 | 44 | 124 | 33.6% |
| Blood Type A2 | 30 | 30 | 17 | 77 | 8.4% |
| Blood Type B | 30 | 30 | 20 | 80 | 10% |
| Blood Type O | 60 | 60 | 56 | 176 | 44% |
| Blood Type AB | 15 | 15 | 13 | 43 | 4% |
| Blood Type Rh+ | 144 | 144 | 113 | 401 | 85% |
| Blood Type Rh− | 31 | 31 | 37 | 99 | 15% |
| Females | 124 | 124 | 95 | 343 | 51% |
| Males | 51 | 51 | 55 | 157 | 49% |
| Mean Age | 44 | 44 | 41 | 43 | 32 |
| Mean Pulse | 70 | 70 | 69 | 70 | 70 |
| Mean Blood Pressure | 114/76 | 114/76 | 111/73 | 113/75 | 120/80 |
| Mean BMI-Female | 24.2 | 24.2 | 23.2 | 23.9 | 21.5-22.4 |
| Mean BMI-Male | 25.9 | 25.9 | 24.7 | 25.5 | 22-22.7 |

Statistical analysis for Type 1 food allergies (IgE) was compiled in the following manner: Reactivity was determined by mean antibody scores for each of 34 foods, and analyzed as continuous data. Subjects were grouped by blood type (A1, A2, B, O, AB, Rh+ and Rh−), and by gender. Bartlett's test, plus graphs of the means verses standard deviation, indicated a lack of homogeneity. Data was log (X+1) transformed, and homogeneity confirmed by Bartlett's test. (Barlett's test was performed by SAS, Statistical Analysis System, on IBM mainframe). The P values were determined on the transformed data by ANOVA (analysis of variance, performed by Statview for Macintosh). Significance was set at 0.05. P values of <0.1 were reported to allow for the small sample of blood type AB. Results were reported for 5950 food test scores; these showed the highest IgE allergies for blood types B and Rh-negative.

Statistical analysis for Type 3 food hypersensitivities (IgG) was compiled in the following manner: (An adjustment was used to equalize the varying blanks used by the lab.) Reactivity was determined by mean antibody scores for each of 34 foods, and analyzed as continuous data. Subjects were grouped by blood type (A1, A2, B, O, AB, Rh+ and Rh−), and by gender. Bartlett's test, plus graphs of the means verses standard deviation, indicated a lack of homogeneity, both before and after most log (X+1) transformations. (Barlett's test was performed by SAS, Statistical Analysis System, on IBM mainframe.) Based on results, the p value was then determined by nonparametric methods: Kruskal-Wallis (3+ factors) and Mann-Whitney U (2 factors). (These were performed by Statview for Macintosh.) Significance was set at 0.05. P values of <0.1 were reported to allow for the small sample of blood type AB. Results were reported for 5950 food test scores; these showed the highest IgG hypersensitivites for blood types O and A2.

Statistical analysis for Type 4 food hypersensitivities (T-Cell) was compiled in the following manner: Strong and immediate reactions were weighted the same, and analyzed as binary data. (Data was analyzed by SAS, Statistical Analysis System, on IBM). Reactivity was determined by percentage of subjects reactive to each of 200 foods. Subjects were grouped by blood type (A1, A2, B, O, AB, Rh+ and Rh−), and by gender. Variations in food response were analyzed by Chi-square (likelihood ratio), and Fisher's Exact Test (2-tail). Variations in food-group reactions were analyzed by Multivariate ANOVA. Signficance for alpha was set at <0.05. P values of <0.1 were reported to allow for the small sample of blood types A2, B, AB (less than 30 foods). Foods were also reported as reactive if they reacted with more than 34% of a specific blood type. Results were reported for 30,000food test scores; these showed the highest T-cell hypersensitivities for blood type B. This made 41,900 food test scores analyzed in total.

Example 2b

Interpretation of the Data

Identifying patterns in food allergies relative to blood types or gender was determined by the strength of the reactions (mean test scores) and by statistical significance (p values).

Establishing classes for the degree of human clinical immune reactivity to foods is problematic in three ways: (1) assigning classes to frequency distributions (ranges) of continuous variables is arbitrary, (2) groups have less extreme ranges than individuals, and (3) the frequency distribution represents a range of healthy to unhealthy food reactions, rather than bivariate normal distribution. Therefore, the preferred method of classification was to apply non-bivariate divisions to the distribution of test scores in each study. Hence the lower ⅓ of food scores was designated as non-reactive (0-33%). The middle ⅓ was designated as equivocal (34%-67%). And the upper ⅓ was designated as reactive (67%-100%). Additional classifications were used at the median (50%), and at (84%). These classifications are comparable to conventional lab values of food allergy tests at the lower ranges, which begin at similar values for modified RAST (500 IgE and 1500 IgG). These non-bivariate divisions were used to establish descriptive classifications and numeric classifications (as shown in Table 1), with six categories. This classification was applied to the range of raw scores for both IgE and IgG. Given that the T-cell test is qualitative, the responses were calculated based on the number of subjects reactive to a given food. The resulting percentages were ranked according to non-bivariate divisions. (Sokal & Rohlf, Introduction to Biostatistics, Freeman, N.Y., 1987.)

Estimating the degree of human clinical immune reactivity to lectins was determined by assigning a percentage and Class value to lectin-containing foods. ABO-specific lectins are known to cause tissue damage, but are not as "severe" as IgE reactions. Therefore they were assigned to the "strong" category (Class 3) at 75%. Similarly, panhemagglutinins are lectins that react with all blood types, and can cause tissue damage, but do not cause strong reactive symptoms in all people. These were assigned to the non-reactive category (Class 0) at 25%.

For the Food Allergy Index and Food Allergy Pyramid the raw test scores (of IgE, IgG, T-cells, and lectins) were converted to percentages, and the percentages of all four kinds of hypersensitivities were summed to provide a total score for each food. A classification system (based on non-bivariate divisions) was applied to the range of total scores. In the Food Allergy Pyramid the foods were grouped into fifteen food groups.

TABLE 3

BLOOD TYPE A1: FOOD ALLERGY SCORES
Allergic Foods In Descending Order, Lectins Alphabetic

| TYPE 1 IgE Allergies | TYPE 2 Lectins | TYPE 3 IgG Allergies | TYPE 4 T-Cell Allergies |
|---|---|---|---|
| Extreme-5 | Strong-3 | Extreme-5 | Strong-3 |
| 1500 | Beans: African Yam | 4800 | Corn syrup 77% |
| Severe-4 | Beans: field | Severe-4 | Cheese 68% |
| 1250 | Beans: lima | Eggwhite 4059 | Corn 68% |
| Strong-3 | Beans: soya | Strong-3 | Milk-Cow 68% |
| 1000 | Beans: string | Eggyolk 3502 | Moderate-2 |
| Moderate-2 | Beans: tora | Milk 3450* | Chocolate 66% |
| 750 | Beans: winged | Moderate-2 | Eggplant 66% |
| Mild-1 | Blackberries | Cheese 2850 | Coffee 64% |
| Soy 596 | Brown trout | Mild-1 | Peanut 64% |
| Almond 529 | Clam: giant butter | Rye 2273 | Butter 61% |
| Orange 525 | Cornflakes | Pineapple 2151 | Casein 61% |
| Potato 520 | Escargot | Wheat 2149 | Orange 61% |
| Peanut 512 | Garfish | Orange 1941 | Tomato 61% |
| Cashew 506 | Horsegram | Banana 1859* | Yeast 61% |
| Bell Pepper 505 | Moluccella Seed | Cashew 1857 | Cottonseed Oil 57% |
| | Mushrooms: Common snow white (*hygrophorus hypothejus*) | Bell Pepper 1760 | MSG 57% |
| | | Almond 1725 | Beet sugar 55% |
| | | Chocolate 1677* | Potato 55% |
| | Peanut (hog) | Rice 1622 | Soy 53% |
| | Product 19 | | Cayenne 52% |
| | Soybean sprouts | | Tea 52% |
| | Total cereal | | Bell pepper 50% |
| | Turtle: western painted | | Food coloring 50% |
| | Vetch: common | | Mild-1 |
| | White croaker fish | | Beef 48% |
| | | | Cane Sugar 48% |
| | | | Wheat 48% |
| | | | Shrimp 45% |
| | | | Baking Powder 43% |
| | | | Chicken 43% |
| | | | Maple 39% |
| | | | Cantaloupe 36% |
| | | | Banana 34% |
| | | | Lobster 34% |

*Significant, p < .06

TABLE 4

BLOOD TYPE A2: FOOD ALLERGY SCORES
Allergic Foods In Descending Order, Lectins Alphabetic

| TYPE 1 IgE Allergies | TYPE 2 Lectins | TYPE 3 IgG Allergies | TYPE 4 T-Cell Allergies |
|---|---|---|---|
| Extreme-5 | Strong-3 | Extreme-5 | Strong-3 |

TABLE 4-continued

BLOOD TYPE A2: FOOD ALLERGY SCORES
Allergic Foods In Descending Order, Lectins Alphabetic

| TYPE 1<br>IgE Allergies | TYPE 2<br>Lectins | TYPE 3<br>IgG Allergies | TYPE 4<br>T-Cell Allergies |
|---|---|---|---|
| 1500 | Beans: African Yam | 4800 | Cheese 82% |
| Severe-4 | Beans: field | Severe-4 | Corn syrup 82% |
| 1250 | Beans: lima | Egg White 4613 | Milk-Cow 82% |
| Strong-3 | Beans: soya | Milk 4413 | Tomato 82% |
| 1000 | Beans: string | Strong-3 | Butter 76% |
| Moderate-2 | Beans: tora | Egg Yolk 3941 | Casein 76% |
| 750 | Beans: winged | Wheat 3196 | Chocolate 71% |
| Mild-1 | Blackberries | Moderate-2 | Corn 71% |
| Soy 612 | Brown trout | Cheese 2862 | Eggplant 71% |
| Peanut 541 | Cornflakes | Chocolate 2841* | Yeast 71% |
| Egg White 515 | Escargot | Rye 2773 | Moderate-2 |
| | Garfish | Soy 2584* | Beet sugar 65% |
| | Moluccella Seeds | Peanut 2556* | Cane sugar 65% |
| | Mushrooms: | Mild-1 | Orange 65% |
| | Common snow white | Cashew 2039 | Cayenne 59% |
| | (*amanita muscaria*) | Oats 2015 | Coffee 59% |
| | (*hygrophorus hypothejus*) | Orange 2001 | Cottonseed Oil 59% |
| | Peanut (hog) | Crab 1891 | Bell pepper 53% |
| | Product 19 | Flounder 1877 | Peanut 53% |
| | Soybean sprouts | Beef 1737 | Potato 53% |
| | Total cereal | Pineapple 1734 | Mild-1 |
| | Turtle: western painted | Clam 1733 | Currant 47% |
| | Vetch: common | Pork 1638 | Food Colors 47% |
| | White croaker fish | Almond 1613 | Grapefruit 47% |
| | | | MSG 47% |
| | | | Tea 47% |
| | | | Wheat 47% |
| | | | Candida 41% |
| | | | Hydrogenated Oil 35% |
| | | | Soy 35% |

*Statistically Significant (p < .06)

TABLE 5

BLOOD TYPE B: FOOD ALLERGY SCORES
Allergic Foods In Descending Order, Lectins Alphabetic

| TYPE 1<br>IgE Allergies | TYPE 2<br>B-Lectins | TYPE 3<br>IgG Allergies | TYPE 4<br>T-Cell Allergies |
|---|---|---|---|
| Extreme-5 | Strong-3 | Extreme-5 | Severe-4 |
| 1500 | Alfalfa | 4800 | Beet Sugar 95% |
| Severe-4 | Beans-castor | Severe-4 | Corn Syrup 90% |
| Peanut 1327 | Beans-Cocoa | 4000 | Cane Sugar 85% |
| Soy 1285 | Beans-field | Strong-3 | Strong-3 |
| Strong-3 | Beans-Mung sprouts | Eggwhite 3630 | Casein 80% |
| 1000 | Beans-soy | Eggyolk 3180 | Chocolate 80% |
| Moderate-2 | Black Eyed Peas | Moderate-2 | Cheese 75% |
| 750 | *Coronilla* | Milk-Cow 2921* | Milk-Cow 75% |
| Mild-1 | Crab-Japanese | Rye 2800 | Yeast 75% |
| Almond 707 | Cucumber-wild | Cheese 2575 | Butter 70% |
| Wheat 699 | *Evonymus Europaeus* | Wheat 2568 | Chicken 70% |
| Cashew 661 | Halfmoon fish | Chocolate 2507* | Corn 70% |
| Tuna 615 | Licorice-Indian | Peanut 2495* | MSG 70% |
| Potato 610 | Melon-Bitter Pear | Soy 2454* | Moderate-2 |
| Strawberry 590 | 2 Mushrooms-French | Mild-1 | Eggplant 65% |
| Rice 580 | Opaleye Fish | Pineapple 1853 | Orange 65% |
| Tomato 575 | Peanut | Oats 1844 | Beef 60% |
| Pork 565 | Pomegranate | Crab 1815 | Coffee 60% |
| Pineapple 521 | Salmon | Strawberry 1792 | Cottonseed Oil 55% |
| Oats 516 | Salmon Caviar | Bell Pepper 1607 | Cranberry 55% |
| Milk-Cow 510 | Sesame Seeds | | Soy 55% |
| | Snakes | | Tomato 55% |
| | Trout Caviar | | Cantaloupe 50% |
| | Tuna | | Tea-black 50% |
| | Turtle-Painted | | Mild-1 |
| | Yeast | | Peanut 45 |
| | | | Potato 45 |
| | | | Wheat 45 |

TABLE 7

BLOOD TYPE A1B: FOOD ALLERGY SCORES
Allergic Foods In Descending Order

| TYPE 1<br>IgE Allergies | TYPE 2<br>Lectins | TYPE 3<br>IgG Allergies | TYPE 4 (AB)<br>T-Cell Allergies |
|---|---|---|---|
| Extreme-5 | Strong-3 | Extreme-5 | Strong-3 |
| 1500 | Hyacinth Beans 4800 | Cheese 77% |
| Severe-4 | All Type | Severe-4 | Milk-Cow 77% |
| 1250 | A Lectins | Cashews 4092 | Butter 69% |
| Strong-3 | All Type | Strong-3 | Casein 69% |
| 1000 | A1 Lectins | Egg White 3695 | Moderate-2 |
| Moderate-2 | All Type | Moderate-2 | Beet sugar 62% |
| Cashews 749 | B Lectins | Cheese 3074 | Corn syrup 62% |
| Mild-1 | | Egg Yolk 2990 | Soya 54% |
| 500 | | Milk 2795 | Tea 54% |
| | | Soy 2769 | Yeast 54% |
| | | Chocolate 2512 | Mild-1 |
| | | Mild-1 | Baking Powder 46% |
| | | Clam 2117 | Food Color 46% |
| | | Flounder 2033 | MSG 46% |
| | | Wheat 1915 | Peanut 46% |
| | | Rye 1769 | Shrimp 46% |
| | | Peanut 1655 | Wheat 46% |
| | | | Anchovy 38% |
| | | | Bell Pepper 38% |
| | | | Chicken 38% |
| | | | Chocolate 38% |
| | | | Coffee 38% |
| | | | Corn 38% |
| | | | Cottonseed Oil 38% |
| | | | Crab 38% |
| | | | Cranberry 38% |
| | | | Eggplant 38% |
| | | | Honey 38% |
| | | | Potato 38% |
| | | | Tomato 38% |

TABLE 8

BLOOD TYPE A2B: FOOD ALLERGY SCORES
Allergic Foods In Descending Order

| TYPE 1<br>IgE Allergies | TYPE 2<br>Lectins | TYPE 3<br>IgG Allergies | TYPE 4 (AB)<br>T-Cell Allergies |
|---|---|---|---|
| Extreme-5 | Strong-3 | Extreme-5 | Strong-3 |
| 1500 | Hyacinth Beans 4800 | Cheese 77% |
| Severe-4 | All Type | Severe-4 | Milk-Cow 77% |
| 1250 | A Lectins | 4000 | Butter 69% |
| Strong-3 | All Type | Strong-3 | Casein 69% |
| 1000 | A2 Lectins | Egg White 3915 | Moderate-2 |
| Moderate-2 | All Type | Milk 3904 | Beet sugar 62% |
| Soy 844 | B Lectins | Chocolate 3656 | Corn syrup 62% |
| Mild-1 | | Egg Yolk 3428 | Soya 54% |
| Cashews 661 | | Soy 3246 | Tea 54% |
| Wheat 637* | | Moderate-2 | Yeast 54% |
| Corn 633 | | Wheat 3126 | Mild-1 |
| Strawberry 629 | | Rye 2990 | Baking Powder 46% |
| Egg White 580 | | Orange 2719* | Food Color 46% |
| Peanut 566 | | Flounder 2544 | MSG 46% |
| Shrimp 561 | | Rice 2449* | Peanut 46% |
| Almond 530 | | Mild-1 | Shrimp 46% |
| Oats 516* | | Cheese 2396 | Wheat 46% |
| Chocolate 504 | | Oats 2273* | Anchovy 38% |
| | | Cashews 2158 | Bell Pepper 38% |
| | | Pineapple 2154 | Chicken 38% |
| | | Clam 2116 | Chocolate 38% |
| | | Potato 1960* | Coffee 38% |
| | | Shrimp 1912 | Corn 38% |
| | | Almond 1783 | Cottonseed Oil 38% |
| | | Strawberry 1754 | Crab 38% |
| | | Pork 1724 | Cranberry 38% |
| | | Tuna 1668 | Eggplant 38% |
| | | | Honey 38% |
| | | | Potato 38% |
| | | | Tomato 38% |

*Statistically Significant (p < .07).

TABLE 9

BLOOD TYPE Rh-Negative: FOOD ALLERGY SCORES
Allergic Foods In Descending Order

| TYPE 1<br>IgE Allergies | TYPE 3<br>IgG Allergies | TYPE 4<br>T-Cell Allergies |
|---|---|---|
| Extreme-5 | Severe-4 | Severe-4 |
| Peanut 1599** | Egg White 4002 | 84% |
| Severe-4 | Strong-3 | Strong-3 |
| Soy 1301 | Rye 3730* | Casein 73% |
| Strong-3 | Milk 3684 | Cheese 73% |
| 1000 | Egg Yolk 3601 | Milk-Cow 73% |
| Moderate-2 | Wheat 3396 | Beet Sugar 73% |
| Cashew 745 | Moderate-2 | Corn Syrup 73% |
| Almond 739 | Cheese 2869 | Chocolate 68% |
| Mild-1 | Cashew 2848* | Moderate-2 |
| Potato 645 | Soy 2497 | Butter 62% |
| Wheat 599 | Peanut 2424 | MSG 59% |
| Beef 596 | Mild-1 | Cottonseed Oil 54% |
| Chocolate 593 | Almond 2290 | Yeast 54% |
| Egg White 593 | Orange 2238 | Cane Sugar 51% |
| Rye 587* | Pineapple 2204 | Coffee 51% |
| Pineapple 581 | Banana 2203 | Corn 51% |
| Strawberry 568 | Oats 2197 | Orange 51% |
| Oats 562 | Shrimp 2159* | Mild-1 |
| Bell Pepper 561 | Chocolate 2123 | Food Coloring 46% |
| Egg Yolk 543 | Rice 2004* | Tea 46% |
| Orange 542 | Flounder 1983 | Cranberry 43% |
| Pork 539 | Strawberry 1956 | Maple 43% |
| Clam 536* | Tomato 1868* | Soybean 43% |
| Salmon 531 | Bell Pepper 1808 | Baking Powder 41% |
| Crab 529 | Crab 1791* | *Candida Al.* 41% |
| Tomato 520 | Potato 1763 | Tomato 41% |
| Cantaloupe 516* | Cantaloupe 1712 | Eggplant 38% |
| Rice 515 | Clam 1670 | Peanut 38% |
| Tuna 513 | Beef 1645 | Wheat 35% |
| | Tuna 1615 | |

Reactions for Rh-negative were higher than for Rh-positive for most foods, particularly for IgE. Symptoms were also greater. Reactions should be interpreted by strength or significance.
*Statistically Significant (p < .05).
**Peanut Highly Significant (p < .0005).

Example 10

Data for Males

In general males were reactive to most of the same foods as females, but males had higher antibody titers for IgE and IgG antibodies. However, males reported less symptoms, which could be explained by higher levels of cortisol reported in the scientific literature, which is anti-inflammatory. Reactions for males should be interpreted by strength and statistical significance (that which is consistent), such as soy. There were no gender differences by T-Cell testing. Food lectin responses are not gender specific.

TABLE 10

MALES: FOOD ALLERGY SCORES

Allergic Foods In Descending Order

| TYPE 1<br>IgE Allergies | TYPE 3<br>IgG Allergies |
|---|---|
| Severe-4 | Severe-4 |
| 1250 | Egg White 4306 |
|  | Milk 4278 |
| Strong-3 | Strong-3 |
| Soy 1102** | Egg Yolk 3618 |
| Peanut 1021 | Cheese 3552 |
| Moderate-2 | Moderate-2 |
| 750 | Wheat 3037* |
|  | Rye 2856 |
|  | Soy 2559* |
|  | Chocolate 2427 |

*Statistically significantly higher for males (p < .05).
**Soy is statistically significantly higher for males (p < .024).

Example 11

Data For Females

Females exhibit allergy differences among selective ABO blood types based on IgE and IgG responses. There are no gender differences for T-Cell responses or lectin reactions.

Females A1's are significantly less allergic to dairy products than male A1's by RAST-IgE and RAST-IgG, with only mild scores, and one moderate score for milk.

Female B's are significantly less allergic to eggs than male B's by RAST-IgE, and have only mild to moderate scores. Female B's also have lower titers to milk and cheese than male B's, which are mild to moderate, but non-significant.

Female A1B's are less allergic to milk and cheese than A1B males by RAST-IgE and RAST-IgG, but these are non-significant, although they are mild scores.

TABLE 11

FEMALES: FOOD ALLERGY SCORES

| | TYPE 1<br>IgE Allergies | TYPE 3<br>IgG Allergies |
|---|---|---|
| FEMALE-A1 | | |
| Cheese | 319** | 2318* |
| Milk | 348* | 2826* |
| Egg White | 422 | 3654 |
| Egg Yolk | 343 | 3076 |
| FEMALE-B | | |
| Cheese | 367 | 2163 |
| Milk | 442 | 2772 |
| Egg White | 336* | 3015 |
| Egg Yolk | 297* | 3024 |
| FEMALE-A1B | | |
| Cheese | 287 | 2283 |
| Milk | 321 | 2264 |
| Egg White | 379 | 3657 |
| Egg Yolk | 365 | 3156 |

*Statistically significantly lower for females (p < .04).
**(p < .069).

Example 12

The Food-Allergy Index™

The "Food-Allergy Index" reports a hierarchy of 34 key food allergens, based on a simple algorithm, which calculates the scores of all subjects in the study, and predicts potential allergic reactions for each food for future persons. This has been formulated by converting the raw scores of each of the four food-allergy types (IgE, IgG, Lectins, and T-cells) to percentages of the full range of their test scores in the biotype studies. Then these are summed to provide a total score. A "Class" is assigned to each score based on standard deviations of the total score range. (See interpreting data.) The scores are then ranked from highest to lowest value.

TABLE 12

FOOD ALLERGY INDEX™
34 Key Foods - All Subjects
Based on Percentages of the Range (0-200) - In Descending Order

| FOOD | Class | TOTAL | IgE % | IgG % | Lectin | T-Cell % |
|---|---|---|---|---|---|---|
| Milk | 4 | 192 | 32 | 81 | 0 | 79 |
| Cheese | 4 | 169 | 29 | 61 | 0 | 79 |
| Wheat | 3 | 165 | 32 | 56 | 25 | 52 |
| Peanut | 3 | 163 | 42 | 42 | 25 | 54 |
| Tomato | 3 | 145 | 28 | 29 | 25 | 63 |
| Chocolate | 3 | 140 | 28 | 46 | 0 | 66 |
| Soybean | 3 | 137 | 46 | 45 | 0 | 46 |
| Potato | 3 | 135 | 31 | 31 | 25 | 48 |
| Egg White | 3 | 134 | 31 | 83 | 0 | 20 |
| Egg Yolk | 3 | 134 | 27 | 72 | 0 | 35 |
| Bell Pepper | 2 | 133 | 30 | 33 | 25 | 45 |
| Coffee | 2 | 129 | 23 | 22 | 25 | 59 |
| Rye | 2 | 124 | 28 | 57 | 25 | 14 |
| Orange | 2 | 120 | 27 | 39 | 0 | 54 |
| Banana | 2 | 115 | 25 | 38 | 25 | 27 |
| Corn | 2 | 108 | 26 | 20 | 0 | 62 |
| Grape | 2 | 101 | 27 | 30 | 25 | 19 |
| Strawberry | 2 | 101 | 30 | 33 | 25 | 13 |
| Rice | 1 | 97 | 29 | 36 | 25 | 7 |
| Pineapple | 1 | 95 | 30 | 43 | 0 | 22 |
| Beef | 1 | 92 | 29 | 25 | 0 | 38 |
| Cashew | 1 | 91 | 34 | 44 | 0 | 13 |
| Shrimp | 1 | 91 | 25 | 30 | 0 | 36 |
| Chicken | 1 | 89 | 26 | 19 | 0 | 44 |
| Cantaloupe | 1 | 86 | 26 | 25 | 0 | 35 |
| Crab | 1 | 85 | 27 | 31 | 0 | 27 |
| Flounder | 1 | 83 | 29 | 40 | 0 | 14 |
| Clam | 1 | 80 | 27 | 35 | 0 | 18 |
| Almond | 1 | 74 | 33 | 34 | 0 | 7 |
| Pork | 1 | 72 | 27 | 28 | 0 | 17 |
| Apple | 1 | 71 | 22 | 19 | 0 | 30 |
| Oats | 1 | 71 | 26 | 37 | 0 | 8 |
| Salmon | 0 | 65 | 31 | 24 | 0 | 10 |
| Tuna | 0 | 65 | 27 | 23 | 0 | 15 |

Example 13

The Food-Allergy Pyramid

The "Food-Allergy Pyramid" is based on the Food-Allergy Index above. This is based on a simple algorithm that calculates the total potential allergic reaction of a given food, based on all subjects of the biotype research. Each kind of test (IgE, IgG, Lectin, and T-cell) was normalized to a percentage of its range, then the percentages were added for a "Total" score. Foods were categorized into food groups, then arranged on a pyramid drawing according to descending scores, and divided into predictive categories of mild, moderate, strong, and severe See FIG. 1.

Example 14

The Diet Compass

The Biotype Diets can be represented as a drawing called "The Diet Compass", wherein the five Biotype Diets (for blood types A1, A2, B, O, AB) are superimposed upon a globe and cross, and positioned according to each blood type's highest frequency, and titled according to the respective geographic locations (A1: Euro Diet, A2: Arctic Diet, B: Asian Diet, O: Tropical Diet, and AB: Mid-East Diet), as shown in FIG. 2.

Patentability

This invention meets the criteria for patentability, as it is a useful, novel, and unobvious process. It is based on novel physical criteria of a food-allergy typing-system, employing the formerly unused criteria of blood types with subtypes, food allergies and food hypersensitivities, in novel combinations, with novel uses for diagnosis and treatment of allergies, as well as a Food-Allergy Index and Food-Allergy Pyramid. It is an unobvious invention to most nutritionists or dietitians, because few if any have training in immunology, allergy, or blood group serology. It also provides new and unexpected results reflected in the final diets for each blood type. This system has commercial value, and a strong need with the increase in allergies in the last two decades. The details of the final invention are a trade secret, and have not been known or used by others until less than one year ago. No scientific, commercial, or popular papers have been published containing the final research. No commercial products or sales have been made containing the details as described herein before one year ago. A U.S. provisional patent application was filed on Jul. 15, 2004, and no patents have been applied for elsewhere. Presentations have been made since that time.

CONCLUSIONS, RAMIFICATIONS, AND SCOPE

Accordingly, The Biotype Diets: invention provides a novel method of identifying and predicting potential food allergies and hypersensitivities using a food-allergy-typing system, a method of treating or mitigating the risk of food allergies and hypersensitivities, and a diet-typing system for optimal food selection that employs diet cards for each blood type. The advantages are multiple:
1. It can bypass expensive, dangerous, or time-consuming allergy testing.
2. It can be easily used by millions of people without a doctor's visit.
3. It is inexpensive and easy to do, requiring only a finger-prick test for blood types ABO, A1-A2, and Rh factor.
4. It provides unique diets for each blood type, which reflect new and unexpected results.
5. It provides diets for six types of people, rather than just four.
6. It provides diet modifications for three subtypes.
7. It is based on rigorous scientific research.
8. It is highly specific, because it employs more biological types for criteria: A1, A2, B, O, A1B, A2B, Rh-positive, Rh-negative, male and female.
9. It is highly accurate, because it is based on objective testing, using all four kinds of food allergies and hypersensitivities: IgE antibodies, IgG antibodies, T-cells, and lectins.
10. It is very precise, because clinical categories are based on standard deviations, and correspond well with standard laboratory ranges for food allergies and hypersensitivities.
11. It provides The Diet Compass to summarize and illustrate the diet types.
12. It provides a Food-Allergy Index to compare specific food allergens for all people.
13. It provides a Food-Allergy Pyramid to show a hierarchy of food allergens.
14. In summary it is a significant improvement on past diet-typing systems.

Although the description above contains many specificities, these should not be construed as limiting the scope of the invention, but as merely providing illustrations and examples of the presently preferred embodiments of this invention. For example other uses would constitute a Food-Allergy Index or Food-Allergy Pyramid, or other embodiment. Thus the scope of the invention should be determined by the appended claims and their legal equivalents, rather than by the examples given.

I claim:

1. A method of formulating a "Biotype Food-Allergy System" for the purpose of identifying and predicting potential food allergies, or food hypersensitivities, or adverse immune responses to foods in a human subject, wherein said method comprises:
   (a) Identifying human subjects with specific ABO or Rh blood types, and optionally gender, and selecting for at least two of these blood types;
   (b) Testing said subjects for at least one immune response that is indicative of food allergies (IgE) or food hypersensitivities (IgG, T-Cell) to generate test scores for various foods, and optionally to use these with known hypersensitivities to food lectins;
   (c) Correlating the blood types (and optionally gender) from step (a) to the immune response test scores from step (b) using appropriate statistical methods to develop data;
   (d) Interpreting said data to establish classes for the degree of clinical immune reactivity to foods;
   (e) Identifying patterns in the data (step c) and classes (step d) to formulate a "Biotype Food-Allergy System", which identifies allergenic foods for each blood type, and optionally gender, for the purpose of predicting potential food allergens in a future human subject;
   (g) Optionally, ranking the data (step c) and classes (step d) to formulate "Food-Allergy Indexes" for ABO or Rh blood types, or any combination of said blood types, and optionally gender;
   (h) Optionally, ranking the data (step c) and classes (step d) to formulate a "Food-Allergy Pyramid", which ranks food-groups by allergic potential, and relates to ABO or Rh blood type, or any combination of said blood types, and optionally gender.

2. A method according to claim 1, wherein said blood types are selected from the group consisting of RBC (red blood cell) types A, B, O, AB, and subtypes A1 and A2, and types Rh-positive, and Rh-negative.

3. A method according to claim 1, wherein testing for immune responses that are indicative of food allergies and/or food hypersensitivities are selected from the following: IgE antibody titers of subjects to specified foods; or IgG antibody titers of subjects to specified foods; or T-cell lymphocyte response of subjects to specified foods; and optionally blood-type response to ABO specific lectins in foods.

4. A method according to claim 1, wherein correlation to produce data means the statistical analysis of data as follows:
   (a) To determine the means of food allergy test scores for IgE antibodies or IgG antibodies, or the percentage of reactive subjects for T-cell food hypersensitivity test scores, for specific foods, food groups, and subject groups (blood types, or gender);
   (b) To analyze the statistical significance of scores between said groups using appropriate methods of: ANOVA, MANOVA, and/or non-parametric methods for determining p value, and in the case of lectins a positive haemagglutination reaction.

5. A method according to claim 1, wherein interpreting the data means to estimate the degree of human clinical immune reactivity to foods by evaluating data distributions and establishing clinical classifications, and may include the following:

(a) To determine the ranges of food allergy test scores (IgE, and/or IgG, T-cell) for specific foods, food groups, and subject groups (blood types, or gender);
(b) To analyze the frequency distribution of said test scores for said groups;
(c) To apply clinical classification divisions to each kind of test (IgE, and/or IgG, and/or T-cell), which reflects the non-bivariate nature of food allergy test scores, and may include:
(1) A thirds method, wherein the lower ⅓ of test scores is designated as non-reactive, the middle ⅓ as equivocal, and the upper ⅓ as reactive, (2) or a method employing classifications beginning at the median or mean (50%), (3) or other non-bivariate distribution divisions;
(d) Optionally, to estimate the degree of human clinical immune reactivity to lectins by assigning a percentage or Class value to lectin-containing foods, wherein ABO-specific lectins reflect a strong reaction and may be assigned a value of 75% (Class 3) or other percentage value, and panhemagglutinins reflect a lesser reaction and may be assigned a value of 25% (Class 0) or other percentage value;
(e) Optionally, to convert said test scores and/or Lectin reactions to a common numeric system using an algorithm or percentages, to sum the converted scores to obtain a composite score for any single food or food group, and assign a class value;
(f) To establish a clinical classification table for food allergies & hypersensitivities, which contains classes for the degree of clinical immune reactivity to foods for the data from the IgE, and/or IgG, and/or T-cell, and/or lectin studies, including both descriptive and numeric classifications, such as in the following table:

Clinical Classification Table for Food Allergies & Hypersensitivities

| Class No. | CLINICAL CLASS: Degree of Immune Reactivity | IgE mRAST Antibody Titers | IgG mRAST Antibody Titers | T-Cell ELISA/ACT % Reactive +Subjects | LECTINS | RANGE OF SCORES |
|---|---|---|---|---|---|---|
|   |   | 1700 | 4600 | 100% |   | Maximum |
| 5 | Extreme Reaction | 1450+ | 4050+ | 90%+ |   |   |
| 4 | Severe Reaction | 1200+ | 3500+ | 80%+ |   |   |
| 3 | Strong Reaction | 950+ | 2950+ | 70%+ | 75% ABO Lectins |   |
| 2 | Moderate Reaction | 700+ | 2400+ | 60%+ |   |   |
| 1 | Mild Reaction | 450+ | 1850+ | 50%+ |   | Median Or Mean |
| 0 | Non-reactive | 0 | 0 | 0% | 25% Pan Lectins | Minimum. |

6. A method according to claim 5, of formulating a "Biotype Food-Allergy System", which identifies food allergens for subjects of at least two ABO and/or Rh blood types (and optionally gender), for the purpose of predicting potential food allergens for future people of the same blood types, and comprises the following steps:

(a) For each blood type selected (and optionally gender) calculate mean food allergy scores for each food for each kind of allergy test performed (IgE, and/or IgG, and/or T-cell);
(b) Rank said food allergy scores and estimated lectin scores using the "Clinical Classification Guide for Food Allergies & Hypersensitivities" of claim 5;
(c) Categorize the food allergens to produce separate Biotype Food Allergen Profiles, each containing one set of food allergens for each blood type selected (A1, A2, B, O, AB, A1B, A2B, or Rh-neg), with at least two types selected; wherein each food allergen profile contains a minimum of four foods classified as strong, severe, or extreme; and wherein the combinations of the allergenic foods classified as extreme and/or severe for one blood type are not so classified for other blood types;
(d) Optionally modify said food allergen profiles with allergens relative to gender, or provide a separate profile for gender;
(e) And optionally, record said scores on paper or on another medium.

7. A method according to claim 6, wherein the food allergens that have been identified for blood type A1 subjects, are predictive for other type A1 persons, and comprise the following Biotype A1 Allergen Profile:

(a) CLASS 5, Extreme allergens: Egg white;
(b) CLASS 4, Severe allergens: Egg yolk, milk;
(c) CLASS 3, Strong allergens: Corn syrup;
(d) CLASS 3, Lectins: Blackberries, brown trout, Coronilla herb, escargot, field beans, garfish, giant butter clam, halibut, hog peanut, horse gram, lima beans, 3 mushrooms (snow white mushroom, *Hygrophorus hypothejus, Psilocybe spadicea*), snakes, soybeans, soy sprouts, string beans, tora beans, vetch (common & hairy), western painted turtle, white croaker fish, winged beans;
(e) CLASS 2, Moderate allergens: Butter, casein, cheese, chocolate, coffee, corn, eggplant, orange, peanut, tomato, yeast;
(f) CLASS 1, Mild allergens: Almond, banana, beet sugar, bell-pepper, cashew, cayenne pepper, cottonseed oil, flounder, food coloring, MSG, pineapple, potato, orange, rye, salmon, soy, tea, wheat;
(g) CLASS 0, Non-Allergic: Any other foods not listed as Classes 1-5.

8. A method according to claim 6, wherein the food allergens that have been identified for blood type A2 subjects, are predictive for other type A2 persons, and comprise the following Biotype A2 Allergen Profile:
(a) CLASS 5, Extreme Allergens: Egg white, milk;
(b) CLASS 4, Severe Allergens: Cheese, corn syrup, Egg yolk, tomato;
(c) CLASS 3, Strong Allergens: Butter, casein, chocolate, corn, eggplant, wheat, yeast;
(d) CLASS 3, Lectins: Blackberries, brown trout, escargot, field beans, garfish, halibut, hog peanut, lima beans, 4 mushrooms (snow white mushroom, Amanita muscaria, *Hygrophorus hypothejus, Psilocybe spadicea*), snakes, soybeans, soy sprouts, string beans, torn beans, vetch (common & hairy), western painted turtle, white croaker fish, winged beans;
(e) CLASS 2, Moderate Allergens: Beet sugar, cane sugar, orange, peanut, rye, soy;
(f) CLASS 1, Mild Allergens: Beef bell pepper, cashew, cayenne pepper, coffee, cottonseed oil, crab, flounder, oats, potato;
(g) CLASS 0, Non-Allergic: Any other foods not listed as Classes 1-5.

9. A method according to claim 6, wherein the food allergens that have been identified for blood type B subjects, are predictive for other type B persons, and comprise the following Biotype B Allergen Profile:
(a) CLASS 5, Extreme Allergens: Beet sugar, corn syrup;
(b) CLASS 4, Severe Allergens: Casein, cane sugar, chocolate, egg white, peanut, soy;
(c) CLASS 3, Strong Allergens: Butter, chicken, corn, egg yolk;
(d) CLASS 3, Lectins: Bitter pear melon, black eyed peas, carp-minnow roe, cocoa, Coronilla herb, crab (Japanese), field beans, 3 French mushrooms (*Hygrophorus hypothejus, Marasmius oreades, Psilocybe spadicea*), halfmoon fish, opaleye fish, perch & perch roe, pomegranate, salmon caviar, sesame seed, snakes, soybean (mild), trout caviar, tuna, western painted turtle;
(e) CLASS 2, Moderate Allergens: Almond, beef, cheese, coffee, eggplant, milk, orange, rye, wheat;
(f) CLASS 1, Mild Allergens: Bell pepper; cantaloupe, cashew, cayenne pepper, cottonseed oil, cranberry, MSG, oats, pork, potato, pineapple, rice, salmon, strawberry, tomato, tea, tuna, yeast;
(g) CLASS 0, Non-Allergic: Any other foods not listed as Classes 1-5.

10. A method according to claim 6, wherein the food allergens that have been identified for blood type O subjects, are predictive for other type O persons, and comprise the following Biotype O Allergen Profile:
(a) CLASS 5, Extreme Allergens: Milk;
(b) CLASS 4, Severe Allergens: Casein, cheese, egg white;
(c) CLASS 3, Strong Allergens: Beet sugar, butter, corn syrup, egg yolk, rye, wheat;
(d) CLASS 3, Lectins: Asparagus pea, Australian catfish, blackberries, boa constrictor, cocoa, eels, Evonymous Europaeus (yellow butter dye), French mushrooms (amanita muscaria), gorse, halfmoon fish, halibut, opaleye fish, perch & perch roe, sunflower seeds, white croaker fish;
(e) CLASS 2, Moderate Allergens: Banana, chocolate, coffee, MSG, pineapple, tomato, yeast;
(f) CLASS 1, Mild Allergens: Almond, bell pepper, cashew, chicken, cane sugar, corn, cottonseed oil, cranberry, eggplant, flounder, oat, orange, peanut, potato, rice, salmon, soy, tea;
(g) CLASS 0, Non-Allergic: Any other foods not listed as Classes 1-5.

11. A method according to claim 6, wherein the food allergens that have been identified for blood type AB subjects, are predictive for other type AB persons, and comprise the following Biotype AB Allergen Profile:
(a) CLASS 4, Severe Allergens: Egg white;
(b) CLASS 3, Strong Allergens: Cashew, cheese, chocolate, egg yolk, milk, soy;
(c) CLASS 3, Lectins: All lectins for blood types A2, A2 and B;
(d) CLASS 2, Moderate Allergens: Beet sugar, butter, casein, corn syrup, wheat;
(e) CLASS 1, Mild Allergens: Beef clam, flounder, rye, shrimp, tea, yeast;
(t) CLASS 0, Non-Allergic: Any other foods not listed in Classes 1-4.

12. A method according to claim 6, wherein the food allergens that have been identified for blood type A1B subjects, are predictive for other type A1B persons, and comprise the following Biotype A1B Allergen Profile:
(a) CLASS 5, Extreme Allergens: Cashew;
(b) CLASS 4, Severe Allergens: Egg white;
(c) CLASS 3, Strong Allergens: Cheese, egg yolk;
(d) CLASS 3, Lectins: All lectins for blood types A1, A2 and B;
(e) CLASS 2, Moderate Allergens: Beet sugar, butter, casein, chocolate, corn syrup, milk, soy;
(f) CLASS 1, Mild Allergens: Clam, flounder, tea, wheat, yeast;
(g) CLASS 0, Non-Allergic: Any other foods not listed in Classes 1-5.

13. A method according to claim 6, wherein the food allergens that have been identified for blood type A2B subjects, are predictive for other type A2B persons, and comprise the following Biotype A2B Allergen Profile:
(a) CLASS 4, Severe Allergens: Chocolate, egg white, milk;
(b) CLASS 3, Strong Allergens: Rye, wheat, soy;
(c) CLASS 3, Lectins: All lectins for blood types A1, A2 and B;
(d) CLASS 2, Moderate Allergens: Beet sugar, butter, casein, corn syrup, egg yolk, flounder, orange;
(e) CLASS 1, Mild Allergens: Almond, beef, cantaloupe, cashew, cheese, corn, crab, oats, peanut, pork, rice, shrimp, strawberry, tea, tuna, yeast;
(f) CLASS 0, Non-Allergic: Any other foods not listed in Classes 1-4.

14. A method according to claim 6, wherein the food allergens that have been identified for blood type Rh-negative subjects are predictive for other type Rh-negative persons, and comprise the following Biotype Rh-neg Allergen Profile:
(a) CLASS 5, Extreme Allergens: Peanut;
(b) CLASS 4, Severe Allergens: Egg white, egg yolk, milk, rye, soy;
(c) CLASS 3, Strong Allergens: Beet sugar, casein, cheese, corn syrup, wheat;
(d) CLASS 2, Moderate Allergens: Almond, butter, cashew, chocolate;
(e) CLASS 1, Mild Allergens: Banana, beef, bell pepper, cane sugar, cantaloupe, chicken, clam, crab, coffee, corn, cottonseed oil, flounder, grape, MSG, oats, orange, pineapple, pork, potato, rice, salmon, shrimp, strawberry, tomato, tuna, yeast.

15. A method according to claim 6, wherein the food allergen profiles identified and predicted for specific blood types, may be further modified for sub-types of gender, and comprise the following Biotype Gender Allergen Profiles:
(a) Males, CLASS 3, Strong Allergens: Wheat, Soy;
(b) Females, Type A1, CLASS 2: Only moderate reactions to milk and cheese.
(c) Females, Type B, CLASS 2: Only moderate reactions to milk and cheese.
(d) Females, Type A1B, CLASS 1: Only mild reactions to milk and cheese.

16. A method of using the "Biotype Food-Allergy System", that has been formulated by the method of claim 6, to predict potential food allergens or food hypersensitivities for persons of at least two blood types (A1, A2, B, O, AB, A1B, A2B, or Rh-neg) and optionally gender, by the following process:
(a) Identify one's ABO and/or Rh blood type and/or A1-A2 sub-blood type by a blood test, and optionally one's gender;
(b) Select an appropriate Biotype Food Allergen Profile that corresponds to one's blood type, and optionally one's gender, from said "Biotype Food-Allergy System";
(c) Interpret said Biotype Food Allergen Profiles according to clinical classifications, wherein: Class 5 predicts potential extreme food allergens, Class 4 predicts potential severe food allergens, Class 3 predicts potential strong food allergens, Class 2 predicts potential moderate food allergens, Class 1 predicts potential mild food allergens, Class L predicts potential lectin reactions, and Class 0 predicts potentially non-reactive foods.

17. A method according to claim 5 of formulating "Food-Allergy Indexes", which report a hierarchy of allergenic foods for subjects of at least two ABO and/or Rh blood types, and optionally gender, and comprises the following steps:
(a) For each blood type selected and gender (or combination of said types) convert the mean test scores for each food (from the IgE, and/or IgG, and/or T-Cell studies) and optionally lectin reactions to a common numeric system using an algorithm or percentages (of the range);
(b) Combine the converted scores for each food tested, from the selected immune responses measured, to obtain composite scores for each food;
(c) Assign a "Class" value to the composite scores for each food;
(d) Rank said composite scores in a hierarchy from most allergic to least allergic, or alternately arranging these alphabetically, or arranging these by food group;
(e) And optionally, record said scores on paper or on another medium.

18. A method of using the "Food Allergy Indexes" that have been formulated by the method of claim 17, to report and predict the most allergic foods and least allergic foods for persons of ABO and/or Rh blood types, or combination of said types, and optionally gender, and comprises the following steps:
(a) Select a food from the Food Allergy Index, and determine its composite score and class;
(b) For more detail, select a food from the Food Allergy Index, and determine the score for a specific food allergy or hypersensitivity test (such as IgE, or IgG, or T-cell, or Lectin).

19. A method according to claim 17 of formulating a "Food-Allergy Pyramid", which portrays a pictorial hierarchy of allergenic food groups for subjects with ABO and/or Rh blood types, or any combination of said blood types, and optionally gender, comprising the following steps:
(a) Combine the Food-Allergy Index composite scores for specific foods into scores for food groups (such as: dairy, eggs, meats, seafood, grains, nuts, beans, vegetables, nightshades, fruits, oils, sugars, herbs, additives, or other groups);
(b) Arrange said food groups and scores on a pyramid drawing, which is divided into predictive categories or classes of mild, moderate, strong, severe (or other categories), in a hierarchy of most allergic down to least allergic, as shown in FIG. 1.

20. A method or using the "Food Allergy Pyramid", that has been formulated by the method of claim 19, to report and predict the most allergic food-groups and least allergic food-groups for persons of ABO or Rh blood type, or any combination of said types, and optionally gender, by the following process:
(a) Select a specific predictive category or class of food-group allergens on the Pyramid;
(b) Then select a specific food-group from said class, and determine its score.

* * * * *

UNITED STATES PATENT AND TRADEMARK OFFICE
CERTIFICATE OF CORRECTION

PATENT NO. : 7,601,509 B2
APPLICATION NO. : 11/178666
DATED : October 13, 2009
INVENTOR(S) : Laura W. Power It is certified that error appears in the above-identified patent and that said Letters Patent is hereby corrected as shown below:

Column 1, Line 10, "TIE INVENTION" should be changed to --THE INVENTION--

Column 19, Line 1, Table 6 was omitted and should be added back between Tables 5 and 7;
See page 2 of 2 attached hereto.

Column 28, Line 10, "blood types A2, A2 and B" should be changed to --blood types A1, A2 and B--

Column 30, Line 20, "A method or using" should be changed to --A method of using--

Signed and Sealed this

Ninth Day of February, 2010

David J. Kappos
*Director of the United States Patent and Trademark Office*

TABLE 6
BLOOD TYPE O: FOOD ALLERGY SCORES
Allergic Foods in Descending Order

| TYPE 1<br>IgE Allergies | TYPE 2<br>Lectins | TYPE 3<br>IgG Allergies | TYPE 4<br>T-Cell Allergies |
|---|---|---|---|
| Extreme-5 | Strong-3 | Extreme-5 | Severe-4 |
| 1500 | Asparagus pea | 4800 | Milk 89% |
| Severe-4 | Australian catfish | Severe-4 | Cheese 89% |
| 1250 | Bean: African Yam | Milk-Cow 4519* | Casein 86% |
| Strong-3 | Blackberries | Strong-3 | Strong-3 |
| 1000 | Cocoa | Egg White 3861 | Corn Syrup 79% |
| Moderate-2 | Eels | Egg Yolk 3447 | Beet Sugar 75% |
| 750 | Evonymus Europaeus | Cheese 3202 | Butter 71% |
| Mild-1 | (butter dye) | Moderate-2 | Tomato 68% |
| Milk 564 | French mushroom | Rye 3092 | Moderate-2 |
| Salmon 548* | (amanita muscaria) | Wheat 2996 | Chocolate 66% |
| Cheese 523 | Gorse | Banana 2537** | MSG 66 |
| Soy 518 | Halfmoon fish | Pineapple 2453 | Yeast 64% |
| Flounder 501* | Halibut | Mild-1 | Wheat 61% |
| | Lotus | Cashew 2291 | Coffee 61% |
| | Opaleye fish | Flounder 2270 | Cane Sugar 59% |
| | Sunflower seeds | Rice 2144 | Cottonseed oil 59% |
| | | Orange 2095 | Corn 57% |
| | | Soy 2083 | Eggplant 57% |
| | | Peanut 1993 | Tea 57% |
| | | Oat 1973 | Cranberry 54% |
| | | Chocolate 1957 | Peanut 54% |
| | | Almond 1926 | Mild-1 |
| | | Bell pepper 1880 | Orange 48% |
| | | Potato 1845 | Egg yolk 46% |
| | | Clam 1833 | Bell pepper 45% |
| | | Grape 1828* | Food color 45% |
| | | Shrimp 1807 | Potato 45% |
| | | Strawberry 1632 | Cayenne 41% |
| | | | Maple Syrup 41% |
| | | | Chicken 39% |
| | | | Soy 39% |
| | | | Sodium benz 38% |
| | | | Cantaloupe 36% |

\* Statistically significant, $p < .07$
\*\* Statistically significant, $p < .0002$